US009011918B2

(12) United States Patent
Pattanaik

(10) Patent No.: US 9,011,918 B2
(45) Date of Patent: *Apr. 21, 2015

(54) BIOCOMPATIBLE AND BIODEGRADABLE ELASTOMERIC POLYMERS

(75) Inventor: Asima Pattanaik, Vestavia Hills, AL (US)

(73) Assignee: Evonik Corporation, Parsippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/566,392

(22) Filed: Aug. 3, 2012

(65) Prior Publication Data

US 2012/0301518 A1 Nov. 29, 2012

Related U.S. Application Data

(63) Continuation of application No. 12/463,823, filed on May 11, 2009, now Pat. No. 8,246,991.

(60) Provisional application No. 61/051,987, filed on May 9, 2008.

(51) Int. Cl.
| | | |
|---|---|---|
| *A61K 38/08* | (2006.01) |
| *A61K 47/42* | (2006.01) |
| *C07K 7/06* | (2006.01) |
| *A61K 47/48* | (2006.01) |
| *A61L 27/18* | (2006.01) |
| *A61L 27/22* | (2006.01) |
| *A61L 27/58* | (2006.01) |
| *A61L 31/10* | (2006.01) |
| *A61K 9/00* | (2006.01) |
| *A61K 9/16* | (2006.01) |
| *A61K 47/34* | (2006.01) |

(52) U.S. Cl.
CPC ........... *A61K 47/48192* (2013.01); *A61K 47/42* (2013.01); *A61K 9/0024* (2013.01); *A61K 9/1641* (2013.01); *A61K 47/34* (2013.01); *A61K 47/482* (2013.01); *A61K 47/48246* (2013.01); *A61K 47/48992* (2013.01); *A61L 27/18* (2013.01); *A61L 27/227* (2013.01); *A61L 27/58* (2013.01); *A61L 31/10* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 4,589,882 A | 5/1986 | Urry |
| 4,898,926 A | 2/1990 | Urry |
| 5,243,038 A | 9/1993 | Ferrari et al. |
| 5,514,581 A | 5/1996 | Ferrari et al. |
| 5,606,019 A | 2/1997 | Cappello |
| 5,817,303 A | 10/1998 | Stedronsky et al. |
| 6,380,154 B1 | 4/2002 | Cappello et al. |
| 6,533,819 B1 | 3/2003 | Urry et al. |
| 6,553,819 B1 | 4/2003 | Schernewski et al. |
| 6,632,450 B1 | 10/2003 | Gregory |
| 8,246,991 B2* | 8/2012 | Pattanaik ............... 424/486 |
| 2003/0078339 A1 | 4/2003 | Kiser et al. |
| 2003/0176355 A1 | 9/2003 | Cappello et al. |
| 2004/0078090 A1 | 4/2004 | Binette et al. |
| 2004/0267362 A1 | 12/2004 | Hwang et al. |
| 2006/0099373 A1 | 5/2006 | Dupont et al. |
| 2006/0204445 A1 | 9/2006 | Atala et al. |
| 2006/0257377 A1 | 11/2006 | Atala et al. |
| 2006/0263417 A1 | 11/2006 | Lelkes et al. |
| 2007/0265197 A1 | 11/2007 | Furgeson et al. |
| 2008/0038310 A1 | 2/2008 | Hossainy et al. |
| 2009/0275730 A1 | 11/2009 | Oku et al. |
| 2009/0295022 A1 | 12/2009 | Kumar |

FOREIGN PATENT DOCUMENTS

| | | |
|---|---|---|
| EP | 1422242 A8 | 8/2004 |
| WO | WO-03/064496 A2 | 8/2003 |
| WO | WO-03/072748 A2 | 9/2003 |
| WO | WO-2006/099372 A2 | 9/2006 |
| WO | WO-2007/146228 A2 | 12/2007 |

OTHER PUBLICATIONS

Fossey et al., Conformational energy studies of B-sheets of model silk fibroin peptides. I. Sheets of poly(Ala-Gly) chains; *Biopolymers*, 31(13), pp. 1529-1542 (1991).
Ingwall et al., Polydepsipeptides. III Theoretical conformational analysis of randomly coiling and ordered D depsipeptide chains, *Macromolecules*, 7(5), pp. 598-605 (1974).
Ingwall et al., Polydepsipeptides. 5. Experimental conformational analysis of poly(L-alanyl-L-lactic acid) and related model compounds, *Macromolecules* 9(5), pp. 802-808 (1976).
Ohyama et al., Crystal structure of a depsipeptide, Boc-(Leu-Leu-Lac)3-Leu-Leu-Oet, *Biopolymers*, 58(7), pp. 636-642 (2001).
Mammi et al., Polydepsipeptides. A systematic investigation of guest-host effects, *J. Pept. Sci.* 11(5), pp. 273-277 (2005).
Yoshida et al., Sequential polydepsipeptides as biodegradable carriers for drug delivery systems, *J. Biomed. Mater. Res.*, 24(9), pp. 1173-1184 (1990).
Arad et al., Depsipeptide analogues of elastin repeating sequences: conformational analysis, *Biopolymers* 29, pp. 1651-1668 (1990).
Mammi et al., Polydepsipeptides. 13. Synthesis and 1 H-NMR analysis of collagen model structures, *Int. J. Peptide and Protein Research*, 28(1), pp. 29-44 (1986).
Urry et al., Elastic Protein-based Materials in Tissue Reconstruction; *Annals of the New York Academy of Sciences*, 831, pp. 32-46 (1997).
Urry et al., Elastic protein-based polymers in soft tissue augmentation and generation, *J. Biomater. Sci. Polymer Edn.*, 9(10): pp. 1015-1048 (1998).

(Continued)

*Primary Examiner* — Jeffrey E Russel
(74) *Attorney, Agent, or Firm* — Linda S. Li; Jason S. Ngui

(57) ABSTRACT

Disclosed herein are biocompatible and biodegradable polymers which are useful in tissue engineering, wound healing, coatings, and drug delivery, the polymers comprising one or more ECM-mimetic peptides and one or more biodegradable moieties, wherein the moieties do not comprise an amino acid or residue thereof. Further disclosed herein are methods for making and using the disclosed biocompatible polymers.

15 Claims, No Drawings

(56) References Cited

OTHER PUBLICATIONS

Li, M. et al., "Co-electrospun poly(lactide-co-glycolide), gelatin, and elastin blends for tissue engineering scaffolds," *J Biomed Mater Res Part A*, 2006, 79(4): pp. 963-973.
Stizel et al., "Controlled fabrication of a biological vascular substitute," *Biomaterials*, 2006, 27(7): pp. 1088-1094.
"Copolymers". Kirk-Othmer Encyclopedia of Chemical Technology. 2002, vol. 7, pp. 607-611.
Notification of Transmittal of International Preliminary Report on Patentability issued on Nov. 18, 2010 for Intl. App. No. PCT/US2009/002907, filed May 12, 2009 (Inventor—Pattanaik; Applicant—Surmodics Pharmaceuticals, Inc.
Written Opinion issued on Mar. 16, 2010 for Intl. App. No. PCT/US2009/002907, filed May 12, 2009 (Inventor—Pattanaik; Applicant—Surmodics Pharmaceuticals, Inc.
Supplementary Eurorpean Search Report and Opinion issued on Jun. 8, 2011 for EP Pat. App. No. 09762817.6, which claims prioirity to Intl. App. No. PCT/US2009/002907, filed May 12, 2009 (Inventor—Pattanaik; Applicant—Surmodics Pharmaceuticals, Inc.
Preliminary Amendments filed on Dec. 6, 2010 for EP Pat. App. No. 09762817.6, which claims prioirity to Intl. App. No. PCT/US2009/002907, filed May 12, 2009 (Inventor—Pattanaik; Applicant—Surmodics Pharmaceuticals, Inc.
Reply to Written Opinion and amended claims filed on Jan. 5, 2012 for EP Pat. App. No. 09762817.6, which is national phase of Intl. App. No. PCT/US2009/002907, filed May 12, 2009 (Inventor—Pattanaik; Applicant—Surmodics Pharmaceuticals, Inc.; pp. 1-14).
International Search Report issued on Mar. 16, 2010 for Intl. App. No. PCT/US2009/002907, filed May 12, 2009 (Inventor—Pattanaik; Applicant—Surmodics Pharmaceuticals, Inc.
Notice of Allowance issued Apr. 23, 2012 for U.S. Appl. No. 12/463,823, filed May 11, 2009 (Inventor—Pattanaik; pp. 1-6).
Response after Ex Parte Quayle Action filed on Mar. 1, 2012 for U.S. Appl. No. 12/463,823, filed May 11, 2009 (Inventor—Pattanaik; pp. 1-10).
Ex Parte Quayle Action issued on Dec. 1, 2011 for U.S. Appl. No. 12/463,823, filed May 11, 2009 (Inventor—Pattanaik; pp. 1-4).
Response after Non-Final Office Action filed on Nov. 11, 2011 for U.S. Appl. No. 12/463,823, filed May 11, 2009 (Inventor—Pattanaik; pp. 1-13).
Non-Final Office Action issued on Sep. 16, 2011 for U.S. Appl. No. 12/463,823, filed May 11, 2009 (Inventor—Pattanaik; pp. 1-12).
Communication from EPO issued on Mar. 19, 2012 for EP Pat. App. No. 09762817.6, which is national phase of Intl. App. No. PCT/US2009/002907, filed May 12, 2009 (Inventor—Pattanaik; Applicant—Surmodics Pharmaceuticals, Inc.; pp. 1-3).
Response to Communication from EPO filed on Oct. 1, 2012 for EP Pat. App. No. 09762817.6, which is national phase of Intl. App. No. PCT/US2009/002907, filed May 12, 2009 (Inventor—Pattanaik; Applicant—Surmodics Pharmaceuticals, Inc.; pp. 1-14).
Summons to attend oral proceedings issued on Nov. 7, 2012 for EP Pat. App. No. 09762817.6, which is national phase of Intl. App. No. PCT/US2009/002907, filed May 12, 2009 (Inventor—Pattanaik; Applicant—Surmodics Pharmaceuticals, Inc.; pp. 1-3).

* cited by examiner

SEQUENCE LISTING

<160> NUMBER OF SEQ ID NOS: 91

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence; note = synthetic construct

<400> SEQUENCE: 1

Val Pro Gly Val Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Val Pro Gly Gly Val
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Val Pro Val Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Gly Pro Gly Val Val
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Gly Pro Val Gly Val
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Gly Pro Val Val Gly
1               5

<210> SEQ ID NO 7
<211> LENGTH: 5

```
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Pro Val Gly Val Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Pro Val Gly Gly Val
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Pro Val Val Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Pro Gly Gly Val Val
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Pro Gly Val Gly Val
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12

Pro Gly Val Val Gly
```

```
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Val Gly Pro Val Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14

Val Gly Pro Gly Val
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 15

Val Val Pro Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 16

Gly Gly Pro Val Val
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 17

Gly Val Pro Gly Val
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence; note =
``` synthetic construct

<400> SEQUENCE: 18

Gly Val Pro Val Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Val Gly Val Pro Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

Val Gly Gly Pro Val
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Val Val Gly Pro Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 22

Gly Gly Val Pro Val
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 23

Gly Val Gly Pro Val
1               5

<210> SEQ ID NO 24

```
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 24

Gly Val Val Pro Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 25

Val Gly Val Gly Pro
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 26

Val Gly Gly Val Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 27

Val Val Gly Gly Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 28

Gly Gly Val Val Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29
```

```
Gly Val Gly Val Pro
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 30

Gly Val Val Gly Pro
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 31

Val Pro Gly Val Gly Val Pro Gly Val Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 32

Val Pro Gly Gly Val Val Pro Gly Gly Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 33

Val Pro Val Gly Gly Val Pro Val Gly Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 34

Gly Pro Gly Val Val Gly Pro Gly Val Val
1               5                   10

<210> SEQ ID NO 35
<211> LENGTH: 10
<212> TYPE: PRT
<213> ORGANISM: Artificial Sequence
<220> FEATURE:
```

```
<223> OTHER INFORMATION: Description of Artificial Sequence; note =
      synthetic construct

<400> SEQUENCE: 35

Gly Pro Val Gly Val Gly Pro Val Gly Val
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 36

Gly Pro Val Val Gly Gly Pro Val Val Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 37

Pro Val Gly Val Gly Pro Val Gly Val Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 38

Pro Val Gly Gly Val Pro Val Gly Gly Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 39

Pro Val Val Gly Gly Pro Val Val Gly Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 40

Pro Gly Gly Val Val Pro Gly Gly Val Val
1               5                   10
```

```
<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 41

Pro Gly Val Gly Val Pro Gly Val Gly Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 42

Pro Gly Val Val Gly Pro Gly Val Val Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 43

Val Gly Pro Val Gly Val Gly Pro Val Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 44

Val Gly Pro Gly Val Val Gly Pro Gly Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 45

Val Val Pro Gly Gly Val Val Pro Gly Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 46
```

```
Gly Gly Pro Val Val Gly Gly Pro Val Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 47

Gly Val Pro Gly Val Gly Val Pro Gly Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 48

Gly Val Pro Val Gly Gly Val Pro Val Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 49

Val Gly Val Pro Gly Val Gly Val Pro Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 50

Val Gly Gly Pro Val Val Gly Gly Pro Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 51

Val Val Gly Pro Gly Val Val Gly Pro Gly
1               5                   10

<210> SEQ ID NO 52
<211> LENGTH: 10
<212> TYPE: PRT
<213> ORGANISM: Artificial Sequence
```

```
<220> FEATURE:
<223> OTHER INFORMATION: Description of Artificial Sequence; note =
      synthetic construct

<400> SEQUENCE: 52

Gly Gly Val Pro Val Gly Gly Val Pro Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 53

Gly Val Gly Pro Val Gly Val Gly Pro Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 54

Gly Val Val Pro Gly Gly Val Val Pro Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 55

Val Gly Val Gly Pro Val Gly Val Gly Pro
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 56

Val Gly Gly Val Pro Val Gly Gly Val Pro
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 57

Val Val Gly Gly Pro Val Val Gly Gly Pro
1               5                   10
```

```
<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 58

Gly Gly Val Val Pro Gly Gly Val Val Pro
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 59

Gly Val Gly Val Pro Gly Val Gly Val Pro
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 60

Gly Val Val Gly Pro Gly Val Val Gly Pro
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 61

Gly Val Pro Gly Val Gly Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 62

Pro Gly Val Pro Gly Val Gly Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct
```

```
<400> SEQUENCE: 63

Gly Val Pro Gly Val Gly Leu Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 64

Val Gly Val Pro Gly Val Gly Ile Gly
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 65

Gly Val Gly Val Pro Gly Val Gly Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 66

Gly Val Pro Gly Val Gly Leu Leu
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 67

Gly Gly Gly Val Pro Gly Val Gly Gly Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 68

Gly Gly Val Pro Gly Val Gly Gly Ala Ala
1               5                   10

<210> SEQ ID NO 69
<211> LENGTH: 11
<212> TYPE: PRT
```

```
<213> ORGANISM: Artificial Sequence
<220> FEATURE:
<223> OTHER INFORMATION: Description of Artificial Sequence; note =
      synthetic construct

<400> SEQUENCE: 69

Pro Pro Gly Val Pro Gly Val Gly Gly Pro
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 70

Ala Val Pro Gly Val Gly Ala
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 71

Ala Ala Val Pro Gly Val Gly Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 72

Ala Val Pro Gly Val Gly Ala Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 73

Ala Ala Val Pro Gly Val Gly Ala Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 74

Ala Leu Ala Val Pro Gly Val Gly Ala
1               5
```

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 75

Ala Val Pro Gly Val Gly Ala Ile Ile
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 76

Gly Val Gly Val Pro Gly Val Gly Gly Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 77

Ala Ala Val Pro Gly Val Gly Ala Ala Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 78

Ala Ala Ala Val Pro Gly Val Gly Ala Ala Ala
1               5                   10

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 79

Val Pro Gly Gly
1

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

```
<400> SEQUENCE: 80

Ala Pro Gly Val Gly Val
1               5

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 81

Val Pro Gly Gly
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 82

Gly Xaa Xaa Pro
1

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 83

Gly Xaa Gly Val Pro
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 84

Val Pro Gly Xaa Gly
1               5

<210> SEQ ID NO 85
<211> LENGTH: 6
<212> TYPE: PRT
<213> ORGANISM: Artificial Sequence
```

```
<220> FEATURE:
<223> OTHER INFORMATION: Description of Artificial Sequence; note =
      synthetic construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 85

Gly Val Gly Val Xaa Pro
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 86

Gly Ala Gly Ala Gly Ser
1               5

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 87

Val Pro Gly Val
1

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 88

Val Pro Gly Val Gly Val Pro Gly Val Gly Val Pro Gly Val Gly
1               5                   10                  15

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 89

Val Pro Gly Val Gly Val Pro Gly Val Gly Val Pro Gly Val Gly Val
1               5                   10                  15

Pro Gly Val Gly
            20

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence; note =
```

```
                        synthetic construct

<400> SEQUENCE: 90

Val Pro Gly Val Gly Val Pro Gly Val Gly Val Pro Gly Val Gly Val
1               5                   10                  15

Pro Gly Val Gly Val Pro Gly Val Gly
            20                  25

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 91

Pro Leu Gly Gly Val Gly Val Pro
1               5
```

BIOCOMPATIBLE AND BIODEGRADABLE ELASTOMERIC POLYMERS

CROSS REFERENCE TO RELATED APPLICATIONS

This application is a continuation of and claims priority to U.S. application Ser. No. 12/463,823, filed on May 11, 2009 now U.S. Pat. No. 8,246,991, which claims the benefit of U.S. Provisional Application No. 61/051,987, filed May 9, 2008, applications which are incorporated by reference herein in their entirety.

FIELD

Disclosed herein are biocompatible and biodegradable polymers comprising one or more ECM-mimetic peptides. Further disclosed herein are methods for making and using the disclosed biocompatible polymers.

BACKGROUND

Extracellular matrix (ECM) proteins are important modulators of the cellular microenvironment. The interaction of cell-ECM is critical in regulation of cellular functions such as adhesion, migration, proliferation and differentiation. The disruption of cell-ECM structure affects the functionality of the cell and, hence, may result in apoptosis. Because of this reason, the naturally-occurring ECM proteins have been considered in medical applications such as tissue engineering and wound healing. Although the size of naturally-occurring ECM proteins ranges to upwards of several hundreds of kilodaltons, the functionality of these proteins arises generally from the presence of specific peptide sequences that are present within the ECM protein. One or more such sequences may be present and repeated through the ECM protein. As one example, a repeating pentapeptide sequence of Val-Pro-Gly-Val-Gly [SEQ ID NO:1] in elastin, the second most common ECM protein, attributes to its elasticity. Therefore, the polymers of these pentapeptides are reported to have potential in medical application. (See, Dan W. Urry and Asima Pattanaik, "Elastic Protein-based Materials in Tissue Reconstruction," *Artificial Organs,* 831:32-46, 1997, and Dan W. Urry, Asima Pattanaik, Jie Xu, T. Cooper Woods, David T. McPherson and Timothy M. Parker, "Elastic Protein-based Polymers in Soft Tissue Augmentation and Generation," *J. Biomater. Sci. Polymer Edn.,* 9(10):1015-1048, 1998.)

The biological half-life of elastin protein is in the order of 70 years. The polymer containing pentapeptide, Val-Pro-Gly-Val-Gly, [SEQ ID NO:1] is expected to remain in a folded state at biological temperature hence it is also naturally resistant to the proteolytic degradation. It would be most advantageous for any scaffolding material to have the capacity to degrade once the natural tissue has been reconstructed at the site and the presence of the polymer is no longer needed. Therefore, addition of a degradable moiety or functionality to such polymers would have great potential for applications such as tissue engineering; wound healing, coatings, and drug delivery. By controlling the frequency and degradation half-life of the degradable functionality, these polymers can be engineered to have half-lives from a few days to years.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to biocompatible polymers comprising:
 a) one or more ECM-mimetic peptides; and
 b) one or more biodegradable moieties, wherein the moieties do not comprise an amino acid or residue thereof;
wherein the polymers have a weight average molecular weight of from about 1,000 Da to about 2,000,000 Da. Also disclosed are methods for using the disclosed biocompatible polymers. Further disclosed are methods for preparing the disclosed biocompatible polymers.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, devices, and methods described herein can be understood more readily by reference to the following detailed description of specific aspects of the disclosed subject matter and the Examples included therein.

Before the present copolymers, polymer admixtures, compounds, compositions, and/or methods are disclosed and described, it is to be understood that the aspects described herein are not limited to specific compounds, synthetic methods, or uses as such can, of course, vary. It is also to be understood that the terminology used herein is for the purpose of describing particular aspects only and, unless specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

By "contacting" is meant the physical contact of at least one substance to another substance.

By "sufficient amount" and "sufficient time" means an amount and time needed to achieve the desired result or results, e.g., dissolve a portion of the polymer.

Biological and Chemical Definitions

A weight percent of a component, unless specifically stated to the contrary, is based on the total weight of the formulation or composition in which the component is included.

"Biocompatible" as used herein means the biological response to the material or device is appropriate for the device's intended application in vivo. Any metabolites of these materials should also be biocompatible.

"Amino acid" as used herein means α-amino acids (as identified as standard amino acids in Voet and Voet, Biochemistry, John Wiley and Sons, 1990) including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, and also β- and γ-amino acids.

"Biodegradable" generally refers to a biocompatible material that will degrade or erode under physiologic conditions to smaller units or chemical species that are, themselves, biocompatible or non-toxic to the subject and capable of being metabolized, eliminated, or excreted by the subject.

"Bioactive agent" is used herein to include a compound of interest contained in or on the polymer such as therapeutic or biologically active compounds that may be used internally or externally as a medicine for the treatment, diagnosis, cure, or prevention of a disease or disorder. Examples can include, but are not limited to, drugs, small-molecule drugs, peptides, proteins, oligonucleotides, imaging agents, contrast agents. "Bioactive agent" includes a single such agent and is also intended to include a plurality of bioactive agents including, for example, combinations of two or more bioactive agents.

"Molecular weight" as used herein, unless otherwise specified, refers generally to the relative average molecular weight of the bulk polymer. While in practice molecular weight can be estimated or characterized in various ways, including gel permeation chromatography (GPC) or capillary viscometry, molecular weights referred to herein are as measured by GPC.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Enantiomeric species can exist in different isomeric or enantiomeric forms. Unless otherwise specified, enantiomeric species discussed herein without reference to their isomeric form shall include all various isomeric forms as well as racemic or scalemic mixtures of isomeric forms. For example, reference to lactic acid shall herein include L-lactic acid, D-lactic acid, and racemic or scalemic mixtures of the L- and D-isomers of lactic acid; reference to lactide shall herein include L-lactide, D-lactide, and DL-lactide (where DL-lactide refers to racemic or scalemic mixtures of the L- and D-isomers of lactide); similarly, reference to poly(lactide) shall herein include poly(L-lactide), poly(D-lactide) and poly (DL-lactide); similarly, reference to poly(lactide-co-glycolide) will herein include poly(L-lactide-co-glycolide), poly (D-lactide-co-glycolide), and poly(DL-lactide-co-glycolide); and so on.

The terms "percent (%) sequence similarity," "percent (%) sequence identity," and the like, generally refer to the degree of identity or correspondence between different amino acid sequences of proteins or peptides that may or may not share a common evolutionary origin. Sequence identity can be determined using any of a number of publicly available sequence comparison algorithms, such as BLAST, FASTA, etc. To determine the percent identity between two amino acid sequences, the sequences are aligned for optimal comparison purposes. The percent identity between the two sequences is a function of the number of identical positions shared by the sequences (i.e., percent identity=number of identical positions/total number of positions (e.g., overlapping positions)× 100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 87:2264, 1990, modified as in Karlin and Altschul, Proc. Natl. Acad. Sci. USA 90:5873-5877, 1993. Such an algorithm is incorporated into the NBLAST and XBLAST programs of Altschul et al., J. Mol. Biol. 215:403, 1990. BLAST protein searches can be performed with the XBLAST program, score=100, wordlength=12, to obtain amino acid sequences homologous to protein sequences of the invention. Another non-limiting example of a mathematical algorithm utilized for the comparison of sequences is the algorithm of Myers and Miller, CABIOS 4:11-17, 1988. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. In one embodiment, the percent identity between two amino acid sequences is determined using the algorithm of Needleman and Wunsch (J. Mol. Biol. 48:444-453, 1970), using either a Blossum 62 matrix or a PAM250 matrix, a gap weight of 16, 14, 12, 10, 8, 6, or 4, and a length weight of 1, 2, 3, 4, 5, or 6. Sequence similarity can also be determined by inspection.

As disclosed herein there are numerous variants of proteins and peptides (e.g., ECM-mimetic peptides) that are contemplated herein. In addition to the ECM mimetic peptide variants, there are derivatives of these peptides that also function in the disclosed methods and compositions. Protein variants and derivatives are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than from about 2 to about 6 residues are deleted at any one site within the peptide/protein molecule. These variants can ordinarily be prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Accordingly, recombinant technologies can be used for the production of the disclosed peptides. However, chemical synthesis can be typically used for a relatively short peptide/protein such as the ECM-mimetic peptides disclosed herein. Amino acid substitutions are typically of single amino acid residues, but can occur at a number of different locations at once; insertions usually can be on the order of from about 1 to about 10 amino acid residues; and deletions can range from about 1 to about 30 residues. Deletions or insertions can be made in adjacent pairs, i.e., a deletion of 2 amino acid residues or insertion of 2 amino acid residues. Substitutions, deletions, insertions or any combination thereof may be combined to arrive at a final construct. Substitutional variants are those in which at least one amino acid residue has been removed and a different residue inserted in its place. Such substitutions generally are made in accordance with the following Table 1 and are referred to as "conservative substitutions."

TABLE 1

Amino Acid Substitutions
Original Residue Exemplary Conservative Substitutions, others are known in the art.

Ala ↔ Ser
Arg ↔ Lys; Gln
Asn ↔ Gln; His
Asp ↔ Glu
Cys ↔ Ser
Gln ↔ Asn or Lys
Glu ↔ Asp
Gly ↔ Pro
His ↔ Asn or Gln
Ile ↔ Leu or Val
Leu ↔ Ile or Val
Lys ↔ Arg or Gln
Met ↔ Leu or Ile
Phe ↔ Met, Leu, or Tyr
Ser ↔ Thr
Thr ↔ Ser
Trp ↔ Tyr
Tyr ↔ Trp or Phe
Val ↔ Ile or Leu

Substantial changes in function can be made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, can be accomplished, for example, by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the O-amino groups of lysine, arginine, and histidine side chains (Creighton, Proteins: Structure and Molecular Properties, W. H. Freeman & Co., San Francisco pp. 79-86 (1983), which is incorporated by reference herein for its material on post-translational derivatizations), acetylation of the N-terminal amine and, in some instances, amidation of the C-terminal carboxyl.

It is understood that one way to define the variants, derivatives, and analogs of the peptides and proteins disclosed herein is through defining the variants, derivatives, and analogs in terms of homology/identity to specific known sequences. For example, SEQ ID NO:1 sets forth the particular sequence of an ECM mimetic peptide. Specifically disclosed are variants, derivatives, and analogs of these and other peptides and proteins herein disclosed which have at least 90%, 91%, 92%, 93%, 94%, 95%, 96%, 97%, 98%, or 99% sequence similarity to the stated sequence. Those of skill in the art readily understand how to determine the sequence similarity of two proteins, as is disclosed more fully supra.

It is further understood that there are numerous amino acid and peptide analogs that can be incorporated into the disclosed compositions. For example, there are numerous D amino acids or amino acids which have a different functional substituent then the amino acids described above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson, et al., *Methods in Molec Biol* 77:43-73, 1991, Zoller, *Curr Opin Biotech* 3:348-354, 1992; Ibba, *Biotech & Gen Eng Rev* 13:197-216, 1995, Cahill, et al., *TIBS* 14(10):400-403, 1989; Benner, *TIB Tech* 12:158-163, 1994; Ibba and Hennecke, *Bio/technology* 12:678-682, 1994, all of which are incorporated by reference herein for their material related to amino acid analogs).

It is further contemplated that molecules can be synthesized that resemble the peptides disclosed herein, but which are not connected via a natural peptide linkages. For example, peptide analogs can have linkages for amino acids or amino acid analogs that include —$CH_2NH$—, —$CH_2S$—, —$CH_2$—

CH$_2$—, —CH=CH— (cis and trans), —COCH$_2$—, —CH(OH)CH$_2$—, and —CH$_2$SO— (These and others can be found in Spatola, in Chemistry and Biochemistry of Amino Acids, Peptides, and Proteins, B. Weinstein, eds., Marcel Dekker, New York, p. 267 (1983); Spatola, Vega Data (March 1983), Vol. 1, Issue 3, Peptide Backbone Modifications (general review); Morley, *Trends Pharm Sci* (1980) pp. 463-468; Hudson et al., *Int J Pept Prot Res* 14:177-185, 1979 (—CH$_2$NH—, —CH$_2$CH$_2$—); Spatola et al., *Life Sci*, 38:1243-1249, 1986 (—CH$_2$S—); Hann, *J Chem Soc, Perkin Trans I*, 307-314, 1982 (—CH=CH—, cis and trans); Almquist, et al., *J Med Chem* 23:1392-1398, 1980 (—COCH$_2$—); Jennings-White et al., *Tetrahedron Lett* 23:2533, 1982 (—COCH$_2$—); Szelke et al., European Appln, EP 45665 CA (1982)(—CH(OH)CH$_2$—); Holladay et al., *Tetrahedron Lett* 24:4401-4404, 1983 (—CH(OH)CH$_2$—); and Hruby *Life Sci* 31:189-199, 1982 (—CH$_2$S—); each of which is incorporated by reference herein for its material regarding peptide analogs, mimetics, and non-peptide linkages). Also, it is understood that peptide analogs can have more than one atom between the bond atoms, such as β-alanine, γ-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others. For example, D-amino acids and β-amino acids can be used to generate more stable peptides, because these amino acids are not recognized by peptidases and such. Systematic substitution of one or more amino acids of a consensus sequence with a D- or β-amino acid of the same type (e.g., D-lysine in place of L-lysine or β-alanine in place of alanine) can be used to generate more stable peptides. Cysteine residues can be used to cyclize or attach two or more peptides together. This can be beneficial to constrain peptides into particular conformations (Rizo and Gierasch, *Ann Rev Biochem* 61:387, 1992).

Reference will now be made in detail to specific aspects of the disclosed materials, compounds, compositions, components, devices, articles, and methods, examples of which are illustrated in the following description and examples, and in the figures and their previous and following description.

Biocompatible Polymers

The disclosed biocompatible polymers have several desirable attributes, for example, elasticity, flexibility, and strength. Thus, they can have modified properties when compared to a naturally occurring ECM-protein, while still undergoing bio-degradation. The ECM-mimetic peptide sequence disclosed herein can be an elastin-mimetic, a fibrinogen-mimetic, a fibroin-mimetic, a silk-mimetic, a collagen-mimetic, a keratin-mimetic, or a mixture of one or more other mimetics together with the aforementioned.

The disclosed biocompatible polymers can comprise:
a) one or more ECM-mimetic peptides; and
b) one or more biodegradable linkers wherein the linker does not comprise an amino acid;

wherein the polymer has a weight average molecular weight of from about 1,000 Da to about 2,000,000 Da. In one embodiment, the polymer has a weight average molecular weight of from about 1,000 Da to about 2,000,000 Da. In another embodiment, the polymer has a weight average molecular weight of from about 1,000 Da to about 20,000 Da. In a further embodiment, the polymer has a weight average molecular weight of from about 1,000 Da to about 10,000 Da. In a yet further embodiment, the polymer has a weight average molecular weight of from about 10,000 Da to about 100,000 Da. In a still further embodiment, the polymer has a weight average molecular weight of from about 10,000 Da to about 50,000 Da. In a yet another embodiment, the polymer has a weight average molecular weight of from about 5,000 Da to about 20,000 Da. While in a yet another embodiment, the polymer has a weight average molecular weight of from about 10,000 Da to about 20,000 Da. In a still yet further embodiment, the polymer has a weight average molecular weight of from about 50,000 Da to about 200,000 Da. In yet further embodiments, the polymer has a weight average molecular weight of from about 100,000 to about 400,000 Da, from about 400,000 to about 800,000 Da, or from about 800,000 to about 2,000,000 Da.

The disclosed ECM-mimetic peptides comprise residues of amino acids, for example, an α-amino acid, a β-amino acid, a γ-amino acid, and the like. In addition, the amino acids can be chiral, for example, (L)-amino aids, (D)-amino acids, racemic mixtures, or mixtures wherein one optical isomer is enhanced, for example, a 60:40 ratio of one enantiomer over the other. In addition, for amino acids that exist in diastereomeric form, inter alia, threonine, any diastereomeric form or mixtures thereof can be used to form the disclosed ECM-mimetic peptides.

One aspect of the disclosed biocompatible polymers relates to polymers having the formula:

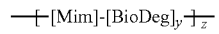

wherein Mim is an ECM-mimetic peptide having the formula:

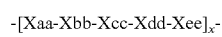

wherein Xaa, Xbb, Xcc, Xdd, and Xee are each independently an amino acid residue chosen from:
i) glycine or a conservative substitution thereof;
ii) valine or a conservative substitution thereof; and
iii) proline or a conservative substitution thereof;
BioDeg is the non-amino acid residue containing biodegradable moiety;
the index x is an integer from 1 to 30;
the index y is an integer from 1 to 10; and
the index z is an integer from 1 to 2000.

In one iteration of this embodiment, the index x is 1. In another iteration, the index x is an integer from 2 to 10. In a further iteration, the index x is an integer from 2 to 6. In a still further iteration, the index x is an integer from 2 to 5. In a still yet further iteration, the index x is an integer from 2 to 4, 5 to 10, 10 to 20, 20 to 30, 15 to 30, 2 to 20, and the like. In another further iteration, the index x is an integer chosen from 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, where any of the stated values can for the upper or lower endpoint of a range. Non-limiting examples of this embodiment includes the index x equal to 4, the index x equal to 5, and the index x equal to 6.

In one iteration of this embodiment, the index y is 1. In another iteration, the index y is an integer from 2 to 6. In a further iteration, the index y is an integer from 3 to 5. In a still further iteration, the index y is an integer from 2 to 5. In a still yet further iteration, the index y is an integer from 2 to 4. In another further iteration, the index y is an integer chosen from 1, 2, 3, 4, 5, 6, 7, 8, 9, or 10, where any of the stated values can for the upper or lower endpoint of a range.

The index z is an integer from 1 to 2000. The index z has a value such that the polymer has a weight average molecular weight of from about 1,000 Da to about 2,000,000 Da. In one embodiment, the index z has a value such that the polymer has a weight average molecular weight of from about 1,000 Da to about 2,000,000 Da. In another embodiment, the index z has a value such that the polymer has a weight average molecular weight of from about 1,000 Da to about 20,000 Da. In a further embodiment, the index z has a value such that the polymer has a weight average molecular weight of from about 1,000 Da to about 10,000 Da. In a yet further embodiment, the index z has a value such that the polymer has a weight average molecular weight of from about 10,000 Da to about 100,000 Da. In a still further embodiment, the index z has a value such that the polymer has a weight average molecular weight of from about 10,000 Da to about 50,000 Da. In a yet another embodiment, the index z has a value such that the polymer has a weight average molecular weight of from about 5,000 Da to about 20,000 Da. While in a yet another embodiment, the index z has a value such that the polymer has a weight average molecular weight of from about 10,000 Da to about 20,000 Da. In a still yet further embodiment, the index z has a value such that the polymer has a weight average molecular weight of from about 50,000 Da to about 200,000 Da.

Another aspect of the disclosed polymers relates to polymers that further comprise a biodegradable or non-biodegradable linking group, L, that serves to link the one or more ECM-mimetic peptides (Mim) and the one or more biodegradable moieties (BioDeg). One embodiment of this aspect relates to polymers having the formula:

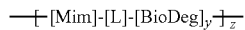

wherein the index y and the index z are as defined herein. Another embodiment of this aspect relates to polymers having the formula:

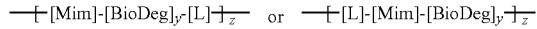

wherein the index y and the index z are as defined herein. A further embodiment of this aspect relates to polymers having the formula:

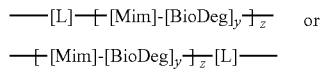

wherein the index y and the index z are as defined herein. A yet further embodiment of this aspect relates to polymers having the formula:

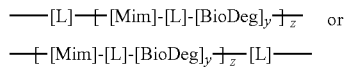

wherein the index y and the index z are as defined herein.

A still further embodiment of this aspect relates to polymers having the formula:

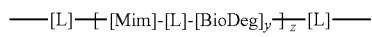

wherein the index y and the index z are as defined herein.

Extracellular Matrix (ECM) Mimetic Peptides

The disclosed biocompatible and/or biodegradable polymers can comprise one or more segments of an ECM-mimetic peptide (identified as "Mim" in the formulae herein)(examples are provided herein). The disclosed one or more ECM-mimetic peptides can be any peptide sequence that repeats throughout an ECM protein and that provides for a characteristic property of the ECM protein. For example, the ECM protein elastin is characterized by a highly elastic property. This elastic property is known to be derived from a peptide sequence that is repeated throughout the protein. In the case of elastin, this repeating peptide sequence provides a characteristic beta-turn structure to the elastin protein. The peptide sequence (the ECM-mimetic peptide sequence) comprises a repeating sequence of 4 or more amino acids based on G, V, and P. Thus, examples of the elastin ECM-mimetic peptide sequence include, but are not limited to, VPGG [SEQ ID NO:81], GxxP [SEQ ID NO:82], GxGVP [SEQ ID NO:83], VPGxG [SEQ ID NO:84], GVGVP [SEQ ID NO:29], GVGVxP [SEQ ID NO:85], and so on where x can be selected from various other amino acids without losing the ECM-mimetic character of this sequence (for example, x can be chosen from valine, lysine, histidine, glutamic acid, arginine, aspartic acid, serine, tryptophan, tyrosine, phenylalanine, leucine, glutamine, asparagine, cysteine, or methionine; x is more preferably valine or lysine). Similarly, the ECM-mimetic peptide sequence for silk can comprise GAGAGS [SEQ ID NO:86]. In keeping with this explanation, an ECM mimetic peptide can described as being an elastin mimetic, a fibrinogen-mimetic, a fibroin-mimetic, a silk-mimetic, a collagen-mimetic, a keratin-mimetic, or a mixture thereof.

In one aspect, the ECM mimetic peptide (Mim) may comprise 3 amino acids, 4 amino acids, 5 amino acids, 6 amino acids, 7 amino acids, and the like. As such, the disclosed biocompatible polymers comprise one or more Mim units, for example, having the formula:

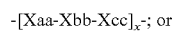

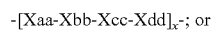

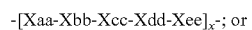

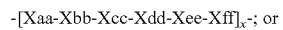

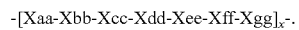

where the amino acids comprising the Mim units are comprised of ECM-mimetic peptide sequences having 3, 4, 5, 6, 7, or more amino acids.

One category of the disclosed biocompatible polymers comprises one or more Mim units having the formula:

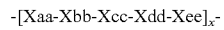

wherein Xaa, Xbb, Xcc, Xdd, and Xee are each independently an amino acid residue chosen from:
 i) glycine or a conservative substitution thereof;
 ii) valine or a conservative substitution thereof; and
 iii) proline or a conservative substitution thereof wherein Xaa, Xbb, Xcc, Xdd, and Xee represent amino acid residues independently chosen from:
 i) glycine or conservative substitutions thereof;
 ii) valine or conservative substitutions thereof; and
 iii) proline or conservative substitutions thereof.

For the purposes of the present disclosure, the conservative substitutions include alanine as a substitute for glycine (Ala for Gly), leucine and isoleucine as substitutes for valine (Leu and Ile for Val), and aziridine-2-carboxylic acid, azetidine-2- carboxylic acid, piperidine-2-carboxylic acid, and piperidine-3-carboxylic acid as substitutes for proline (Aza, Aze, 2-Pip, and 3-Pip for Pro).

In one embodiment of this category wherein the index x is equal to 1, non-limiting examples of ECM-mimetic peptides are chosen from:

i)
[SEQ ID NO: 1]
Val-Pro-Gly-Val-Gly;

ii)
[SEQ ID NO: 2]
Val-Pro-Gly-Gly-Val;

iii)
[SEQ ID NO: 3]
Val-Pro-Val-Gly-Gly;

iv)
[SEQ ID NO: 4]
Gly-Pro-Gly-Val-Val;

v)
[SEQ ID NO: 5]
Gly-Pro-Val-Gly-Val;

vi)
[SEQ ID NO: 6]
Gly-Pro-Val-Val-Gly;

vii)
[SEQ ID NO: 7]
Pro-Val-Gly-Val-Gly;

viii)
[SEQ ID NO: 8]
Pro-Val-Gly-Gly-Val;

ix)
[SEQ ID NO: 9]
Pro-Val-Val-Gly-Gly;

x)
[SEQ ID NO: 10]
Pro-Gly-Gly-Val-Val;

xi)
[SEQ ID NO: 11]
Pro-Gly-Val-Gly-Val;

xii)
[SEQ ID NO: 12]
Pro-Gly-Val-Val-Gly;

xiii)
[SEQ ID NO: 13]
Val-Gly-Pro-Val-Gly;

xiv)
[SEQ ID NO: 14]
Val-Gly-Pro-Gly-Val;

xv)
[SEQ ID NO: 15]
Val-Val-Pro-Gly-Gly;

xvi)
[SEQ ID NO: 16]
Gly-Gly-Pro-Val-Val;

xvii)
[SEQ ID NO: 17]
Gly-Val-Pro-Gly-Val;

xviii)
[SEQ ID NO: 18]
Gly-Val-Pro-Val-Gly;

xix)
[SEQ ID NO: 19]
Val-Gly-Val-Pro-Gly;

xx)
[SEQ ID NO: 20]
Val-Gly-Gly-Pro-Val;

xxi)
[SEQ ID NO: 21]
Val-Val-Gly-Pro-Gly;

xxii)
[SEQ ID NO: 22]
Gly-Gly-Val-Pro-Val;

xxiii)
[SEQ ID NO: 23]
Gly-Val-Gly-Pro-Val;

xxiv)
[SEQ ID NO: 24]
Gly-Val-Val-Pro-Gly;

xxv)
[SEQ ID NO: 25]
Val-Gly-Val-Gly-Pro;

xxvi)
[SEQ ID NO: 26]
Val-Gly-Gly-Val-Pro;

xxvii)
[SEQ ID NO: 27]
Val-Val-Gly-Gly-Pro;

xxviii)
[SEQ ID NO: 28]
Gly-Gly-Val-Val-Pro;

xxix)
[SEQ ID NO: 29]
Gly-Val-Gly-Val-Pro;
and xxx)
[SEQ ID NO: 30]
Gly-Val-Val-Gly-Pro.

In another embodiment of this category wherein the index x is equal to 2, non-limiting examples of ECM-mimetic peptides are chosen from:

i)
[SEQ ID NO: 31]
Val-Pro-Gly-Val-Gly-Val-Pro-Gly-Val-Gly;

ii)
[SEQ ID NO: 32]
Val-Pro-Gly-Gly-Val-Val-Pro-Gly-Gly-Val;

iii)
[SEQ ID NO: 33]
Val-Pro-Val-Gly-Gly-Val-Pro-Val-Gly-Gly;

iv)
[SEQ ID NO: 34]
Gly-Pro-Gly-Val-Val-Gly-Pro-Gly-Val-Val;

v)
[SEQ ID NO: 35]
Gly-Pro-Val-Gly-Val-Gly-Pro-Val-Gly-Val;

vi)
[SEQ ID NO: 36]
Gly-Pro-Val-Val-Gly-Gly-Pro-Val-Val-Gly;

vii)
[SEQ ID NO: 37]
Pro-Val-Gly-Val-Gly-Pro-Val-Gly-Val-Gly;

viii)
[SEQ ID NO: 38]
Pro-Val-Gly-Gly-Val-Pro-Val-Gly-Gly-Val;

ix)
[SEQ ID NO: 39]
Pro-Val-Val-Gly-Gly-Pro-Val-Val-Gly-Gly;

x)
[SEQ ID NO: 40]
Pro-Gly-Gly-Val-Val-Pro-Gly-Gly-Val-Val;

xi)
[SEQ ID NO: 41]
Pro-Gly-Val-Gly-Val-Pro-Gly-Val-Gly-Val;

xii)
[SEQ ID NO: 42]
Pro-Gly-Val-Val-Gly-Pro-Gly-Val-Val-Gly;

xiii)
[SEQ ID NO: 43]
Val-Gly-Pro-Val-Gly-Val-Gly-Pro-Val-Gly;

xiv)
[SEQ ID NO: 44]
Val-Gly-Pro-Gly-Val-Val-Gly-Pro-Gly-Val;

xv)
[SEQ ID NO: 45]
Val-Val-Pro-Gly-Gly-Val-Val-Pro-Gly-Gly;

xvi)
[SEQ ID NO: 46]
Gly-Gly-Pro-Val-Val-Gly-Gly-Pro-Val-Val;

xvii)
[SEQ ID NO: 47]
Gly-Val-Pro-Gly-Val-Gly-Val-Pro-Gly-Val;

xviii)
[SEQ ID NO: 48]
Gly-Val-Pro-Val-Gly-Gly-Val-Pro-Val-Gly;

xix)
[SEQ ID NO: 49]
Val-Gly-Val-Pro-Gly-Val-Gly-Val-Pro-Gly;

xx)
[SEQ ID NO: 50]
Val-Gly-Gly-Pro-Val-Val-Gly-Gly-Pro-Val;

xxi)
[SEQ ID NO: 51]
Val-Val-Gly-Pro-Gly-Val-Val-Gly-Pro-Gly;

xxii)
[SEQ ID NO: 52]
Gly-Gly-Val-Pro-Gly-Gly-Val-Pro-Val;

xxiii)
[SEQ ID NO: 53]
Gly-Val-Gly-Pro-Val-Gly-Val-Gly-Pro-Val;

xxiv)
[SEQ ID NO: 54]
Gly-Val-Val-Pro-Gly-Gly-Val-Val-Pro-Gly;

xxv)
[SEQ ID NO: 55]
Val-Gly-Val-Gly-Pro-Val-Gly-Val-Gly-Pro;

xxvi)
[SEQ ID NO: 56]
Val-Gly-Gly-Val-Pro-Val-Gly-Gly-Val-Pro;

xxvii)
[SEQ ID NO: 57]
Val-Val-Gly-Gly-Pro-Val-Val-Gly-Gly-Pro;

xxviii)
[SEQ ID NO: 58]
Gly-Gly-Val-Val-Pro-Gly-Gly-Val-Val-Pro;

xxix)
[SEQ ID NO: 59]
Gly-Val-Gly-Val-Pro-Gly-Val-Gly-Val-Pro;
and xxx)
[SEQ ID NO: 60]
Gly-Val-Val-Gly-Pro-Gly-Val-Val-Gly-Pro.

Another category of ECM-mimetic peptides includes peptides wherein a particular ECM-peptide mimetic sequence is found within an ECM-peptide that comprises amino acids chosen from glycine, alanine, valine, leucine, isoleucine, and proline, for example:

i)
[SEQ ID NO: 61]
Gly-Val-Pro-Gly-Val-Gly-Gly;

ii)
[SEQ ID NO: 62]
Pro-Gly-Val-Pro-Gly-Val-Gly-Gly;

iii)
[SEQ ID NO: 63]
Gly-Val-Pro-Gly-Val-Gly-Leu-Ala;

iv)
[SEQ ID NO: 64]
Val-Gly-Val-Pro-Gly-Val-Gly-Ile-Gly;

v)
[SEQ ID NO: 65]
Gly-Val-Gly-Val-Pro-Gly-Val-Gly-Gly;

vi)
[SEQ ID NO: 66]
Gly-Val-Pro-Gly-Val-Gly-Leu-Leu;

vii)
[SEQ ID NO: 67]
Gly-Gly-Gly-Val-Pro-Gly-Val-Gly-Gly-Gly;

viii)
[SEQ ID NO: 68]
Gly-Gly-Val-Pro-Gly-Val-Gly-Gly-Ala-Ala;

ix)
[SEQ ID NO: 69]
Pro-Pro-Gly-Val-Pro-Gly-Val-Gly-Gly-Gly-Pro;

x)
[SEQ ID NO: 70]
Ala-Val-Pro-Gly-Val-Gly-Ala;

xi)
[SEQ ID NO: 71]
Ala-Ala-Val-Pro-Gly-Val-Gly-Ala;

xii)
[SEQ ID NO: 72]
Ala-Val-Pro-Gly-Val-Gly-Ala-Ala;

xiii)
[SEQ ID NO: 73]
Ala-Ala-Val-Pro-Gly-Val-Gly-Ala-Ala;

xiv)
[SEQ ID NO: 74]
Ala-Leu-Ala-Val-Pro-Gly-Val-Gly-Ala;

xv)
Ala-Val-Pro-Gly-Val-Gly-Ala-Ile-Ile; [SEQ ID NO: 75]

xvi)
Gly-Val-Gly-Val-Pro-Gly-Val-Gly-Gly-Val; [SEQ ID NO: 76]

xvii)
Ala-Ala-Val-Pro-Gly-Val-Gly-Ala-Ala-Ala; and [SEQ ID NO: 77]

xviii)
Ala-Ala-Ala-Val-Pro-Gly-Val-Gly-Ala-Ala-Ala; [SEQ ID NO: 78]

Another embodiment of this category relates to ECM-mimetic peptides comprising a plurality of receptor sequences. For example, ECM-mimetic peptides having the formulae:

[(Xaa-Xbb-Xcc-Xdd-Xee)]$_3$;

[(Xaa-Xbb-Xcc-Xdd-Xee)]$_4$;

[(Xaa-Xbb-Xcc-Xdd-Xee)]$_5$; or

[(Xaa-Xbb-Xcc-Xdd-Xee)]$_6$;

wherein [(Xaa-Xbb-Xcc-Xdd-Xee)] comprises one or more sequences chosen from:

i)
Val-Pro-Gly-Val-Gly; [SEQ ID NO: 1]

ii)
Val-Pro-Gly-Gly-Val; [SEQ ID NO: 2]

iii)
Val-Pro-Val-Gly-Gly; [SEQ ID NO: 3]

iv)
Gly-Pro-Gly-Val-Val; [SEQ ID NO: 4]

v)
Gly-Pro-Val-Gly-Val; [SEQ ID NO: 5]

vi)
Gly-Pro-Val-Val-Gly; [SEQ ID NO: 6]

vii)
Pro-Val-Gly-Val-Gly; [SEQ ID NO: 7]

viii)
Pro-Val-Gly-Gly-Val; [SEQ ID NO: 8]

ix)
Pro-Val-Val-Gly-Gly; [SEQ ID NO: 9]

x)
Pro-Gly-Gly-Val-Val; [SEQ ID NO: 10]

xi)
Pro-Gly-Val-Gly-Val; [SEQ ID NO: 11]

xii)
Pro-Gly-Val-Val-Gly; [SEQ ID NO: 12]

xiii)
Val-Gly-Pro-Val-Gly; [SEQ ID NO: 13]

xiv)
Val-Gly-Pro-Gly-Val; [SEQ ID NO: 14]

xv)
Val-Val-Pro-Gly-Gly; [SEQ ID NO: 15]

xvi)
Gly-Gly-Pro-Val-Val; [SEQ ID NO: 16]

xvii)
Gly-Val-Pro-Gly-Val; [SEQ ID NO: 17]

xviii)
Gly-Val-Pro-Val-Gly; [SEQ ID NO: 18]

xix)
Val-Gly-Val-Pro-Gly; [SEQ ID NO: 19]

xx)
Val-Gly-Gly-Pro-Val; [SEQ ID NO: 20]

xxi)
Val-Val-Gly-Pro-Gly; [SEQ ID NO: 21]

xxii)
Gly-Gly-Val-Pro-Val; [SEQ ID NO: 22]

xxiii)
Gly-Val-Gly-Pro-Val; [SEQ ID NO: 23]

xxiv)
Gly-Val-Val-Pro-Gly; [SEQ ID NO: 24]

xxv)
Val-Gly-Val-Gly-Pro; [SEQ ID NO: 25]

xxvi)
Val-Gly-Gly-Val-Pro; [SEQ ID NO: 26]

xxvii)
Val-Val-Gly-Gly-Pro; [SEQ ID NO: 27]

xxviii)
Gly-Gly-Val-Val-Pro; [SEQ ID NO: 28]

xxix)
Gly-Val-Gly-Val-Pro; and [SEQ ID NO: 29]

xxx)
Gly-Val-Val-Gly-Pro. [SEQ ID NO: 30]

In another embodiment, the ECM mimetic peptide (Mim) may comprise some number of amino acids other than 5 such as 3 amino acids, 4 amino acids, 6 amino acids, 7 amino acids, and so on. Non-limiting examples include:

i)
Val-Pro-Gly-Gly [SEQ ID NO: 79]
and ii)
Ala-Pro-Gly-Val-Gly-Val. [SEQ ID NO: 80]

The disclosed ECM-mimetic peptides, Mim, and polymers of Mim (i.e., polypeptide):

-[Mim]$_x$- can be made through peptide (chemical) synthetic routes or through microbial synthetic routes or combinations thereof. For example, poly(GVGVP) [SEQ ID NO:29] can be obtained by microbial synthesis. The gene containing the sequence for either [Mim] or for the polymer of Mim, -[Mim]$_x$-, (or poly(GVGVP) [SEQ ID NO:29] protein) has been cloned and expressed in recombinant *E. Coli* host system. After the desired batch of the fermentation, the poly(GVGVP) [SEQ ID NO:29] can be purified from the *E. Coli* lysate.

Biodegradable Moieties

The disclosed biocompatible polymers can comprise one or more biodegradable moieties (identified as "BioDeg" in the formulae herein), wherein the biodegradable moieties do not comprise an amino acid. A first category of biodegradable moieties comprises monomers or homopolymers of hydroxy acids such as lactide, glycolide, valerolactone, hydroxybutyrate, caprolactone, or mixtures thereof. Non-limiting examples of biodegradable moieties, BioDeg, include:

i) Lactic acid;
ii) Glycolic acid;
iii) Lactide (di-lactic acid);
iv) Glycolide (di-glycolic acid);
v) Caprolactone;
vi) hydroxybutyrate;
vii) valerolactone;
viii) a hydroxy acid;
ix) a hydroxy fatty acid;
x) poly(lactide);
xi) poly(glycolide);
xii) poly(caprolactone);
xiii) poly(valerolactone);
xiv) poly(hydroxybutyrate);
xv) poly(lactide-co-glycolide);
xvi) poly(lactide-co-caprolactone);
xvii) poly(lactide-co-valerolactone);
xviii) poly(glycolide-co-caprolactone);
xix) poly(glycolide-co-valerolactone);
xx) poly(lactide-co-glycolide-co-caprolactone); and
xxi) poly(lactide-co-glycolide-co-valerolactone).

The biodegradable moieties, BioDeg, can be bonded directly to the ECM-mimetic peptide (Mim) or can be bonded to the ECM-mimetic peptide (Mim) by a separate bond or linking unit, L, defined herein further.

A first embodiment of this category comprises homopolymers of lactide. This embodiment comprises from 1 to 100 residues of lactide and as such can be represented by the formula:

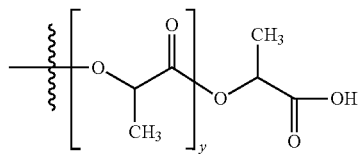

wherein the index y is from is from 0 to 100. In one iteration, the index y is from 1 to 6. In another iteration, the index y is from 2 to 5. In a further iteration, the index y is from 8 to 12. In a yet further iteration, the index y is from 9 to 11. In yet another iteration, the index y is from 10 to 50. In a still further iteration, the index y is from 5 to 15. In a yet still further iteration, the index y is from 20 to 40. However, the homopolymer can comprise any number of monomer units, for example, 1, 2, 3, 4, 5, 6, 7, 8, 9, 10, 11, 12, 13, 14, 15, 16, 17, 18, 19, and 20. Non limiting examples include:

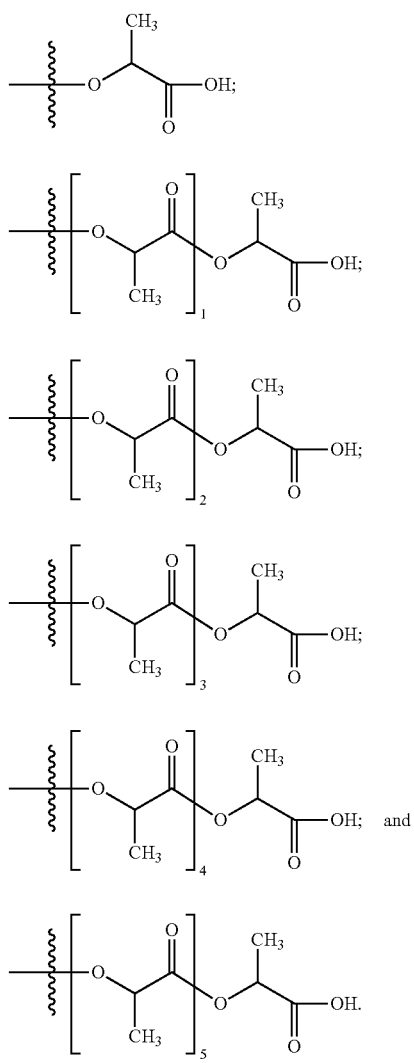

Another embodiment of this category comprises homopolymers of glycolide. This embodiment comprises from 1 to 100 residues of glycolide and as such can be represented by the formula:

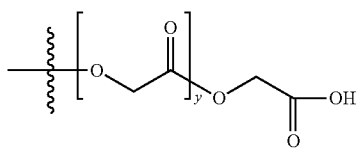

wherein the index y is from is from 0 to 100. In one iteration, the index y is from 1 to 6. In another iteration, the index y is from 2 to 5. In a further iteration, the index y is from 8 to 12. In a yet further iteration, the index y is from 9 to 11. In yet another iteration, the index y is from 10 to 50. In a still further iteration, the index y is from 5 to 15. In a yet still further iteration, the index y is from 20 to 40. However, the homopolymer can comprise any number of monomer units, for example, 1, 2, 3, 4, 5, 6, 7, 8, 9, 10, 11, 12, 13, 14, 15, 16, 17, 18, 19, and 20. Non limiting examples include:

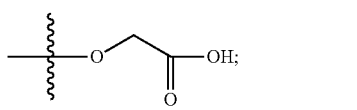

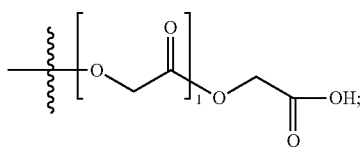

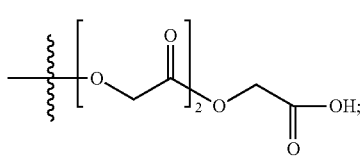

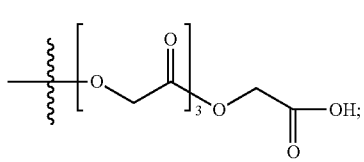

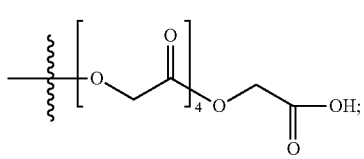

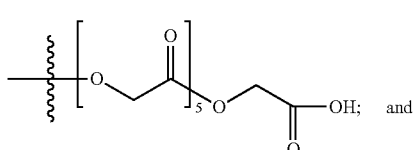

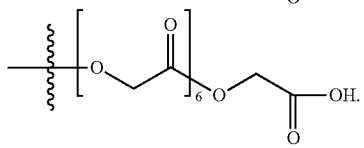

Another embodiment of this category comprises homopolymers of caprolactone. This embodiment comprises from 1 to 100 residues of 6-hydroxyhexanoate and as such can be represented by the formula:

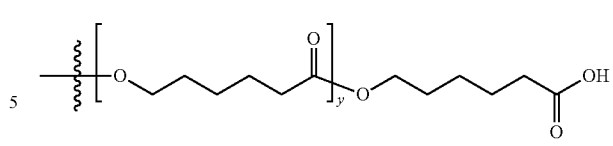

wherein the index y is from is from 0 to 100. In one iteration, the index y is from 1 to 6. In another iteration, the index y is from 2 to 5. In a further iteration, the index y is from 8 to 12. In a yet further iteration, the index y is from 9 to 11. In yet another iteration, the index y is from 10 to 50. In a still further iteration, the index y is from 5 to 15. In a yet still further iteration, the index y is from 20 to 40. However, the homopolymer can comprise any number of monomer units, for example, 1, 2, 3, 4, 5, 6, 7, 8, 9, 10, 11, 12, 13, 14, 15, 16, 17, 18, 19, and 20. Non limiting examples include:

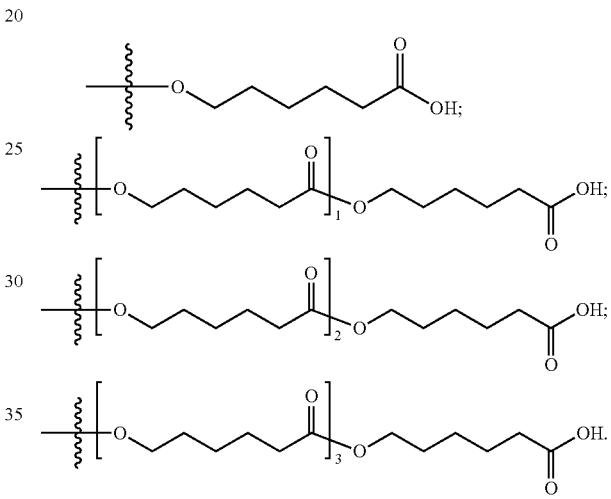

Linking Groups

The disclosed biocompatible polymers can further comprise one or more linking groups. The linking groups, L, can serve to connect an ECM-mimetic peptide (Mim) to a biodegradable moiety (BioDeg), for example, polymers having the formula:

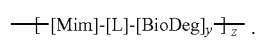

Also the linking groups can serve to connect blocks of ECM-mimetic peptide and biodegradable moieties to other blocks of ECM-mimetic peptide and biodegradable moieties, for example, polymers having the formula:

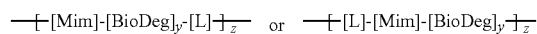

Further the linking groups can serve to both connect a ECM-mimetic peptide to a biodegradable moiety and connect blocks of ECM-mimetic peptides linked to biodegradable moieties to other blocks of ECM-mimetic peptide and biodegradable moieties, for example, polymers having the formula:

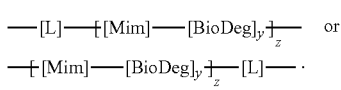

Still further the linking groups can serve to both connect a ECM-mimetic peptide to a biodegradable moiety and connect blocks of ECM-mimetic peptides linked to biodegradable moieties to other blocks of ECM-mimetic peptide and biodegradable moieties, for example, polymers having the formula:

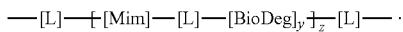

Linking group L can be biodegradable or non-biodegradable. Non-limiting examples of the disclosed linking groups can comprise one or more groups or chemical bonds chosen from:
  i) an alkyl;
  ii) an alkoxy;
  iii) a carbonyl;
  iv) a halogen comprising leaving group;
  v) an ester;
  vi) an orthoester;
  vii) an anhydride;
  viii) a phosphate;
  ix) a phosphazene;
  x) a phosphoester;
  xi) a dioxanaone;
  xii) a carbonate;
  xiii) an orthocarbonate;
  xiv) an amide;
  xv) an amine;
  xvi) an ester amide;
  xvii) a isocyanate;
  xviii) a urethane;
  xix) an etherester;
  xx) a pyrrolidone;
  xxi) or a unit comprising a combination of units (i) to (xx).

In one embodiment, the linking group is formed by a linking reagent that comprises at least one halogen leaving group. For example, a reactive moiety having the formula:

$$X-(CH_2)_t-CO_2H; X-(CH_2)_t-CO_2CH_3; \text{ or } X-(CH_2)_t-COCl$$

wherein X is a halogen leaving group and the index t is an integer from 1 to 10. When fully incorporated into the disclosed polymer, reactive moieties of this type can form linking groups having the formula:

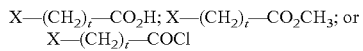

In another embodiment, the linking group can itself be branched or can be multi-functional so as to introduce branching the potential for performing chemical crosslinking to the resulting polymer. For example, a linking group derived from an acid capable of forming a crosslink, inter alia, aspartic acid, glutamic acid, and citric acid. Or the crosslinking unit can be derived from an amino acid, for example, lysine, ornithine, and the like.

In another embodiment, the linking group is formed by a linking reagent that comprises two carbonyl reactive moieties. For example, a reactive moiety having the formula:

$$HO_2C-(CH_2)_t-CO_2H; H_3CO_2C-(CH_2)_t-CO_2CH_3; ClOC-(CH_2)_t-COCl$$

wherein the index t is an integer from 1 to 10. When fully incorporated into the disclosed polymer, reactive moieties of this type can form linking groups having the formula:

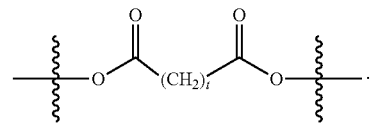

In further embodiment, the linking group is formed by a linking reagent that comprises at least one halogen leaving group. For example, a reactive moiety having the formula:

$$O=C=N-(CH_2)_t-N=C=O$$

wherein the index t is an integer from 1 to 10. When fully incorporated into the disclosed polymer, reactive moieties of this type can form linking groups having the formula:

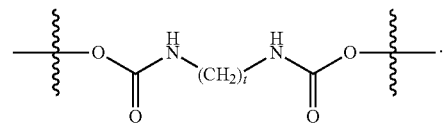

Further embodiments include linking groups having the formulae:

i)

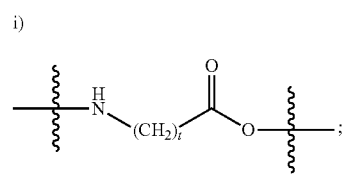

ii)

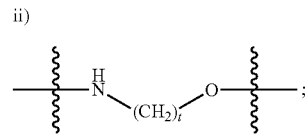

iii)

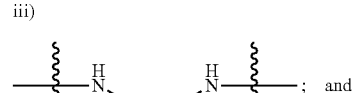; and iv)

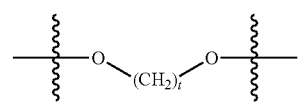

wherein for each the index t is an integer from 1 to 10.

The disclosed polymers can comprise a mixture of linking groups. For example, disclosed polymers having the formula:

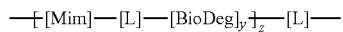

can have a first linking group connecting the one or more ECM-mimetic peptides to the one or more biodegradable moieties thereby forming a block, and a second linking group connecting the plurality of blocks.

SPECIFIC EXAMPLES

One category of the disclosed polymers relates to biocompatible polymers having the formula:

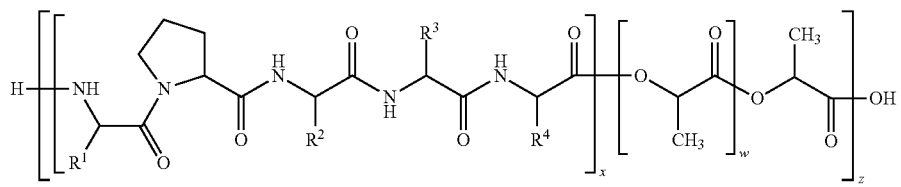

wherein $R^1$, $R^2$, $R^3$, and $R^4$ are each independently chosen from:
  i) hydrogen;
  ii) —$CH_3$;
  iii) —$CH_2CH_3$;
  iv) —$CH_2CH_2CH_3$;
  v) —$CH(CH_3)_2$;
  vi) —$CH(CH_3)CH_2CH_3$; and
  vii) —$CH_2CH_2CH(CH_3)_2$;
the index w is an integer from 0 to 9; the index x is an integer from 1 to 30; and the index z is an integer from 1 to 2000.

One embodiment relates to biocompatible polymers having the formula and which formula includes the ECM an ECM mimetic as set forth in SEQ ID NO: 4:

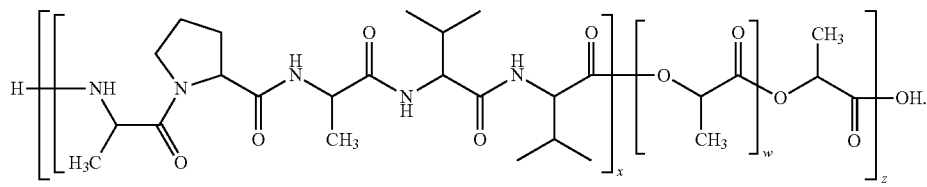

Non-limiting examples of this embodiment include (each comprising SEQ ID NO: 4):

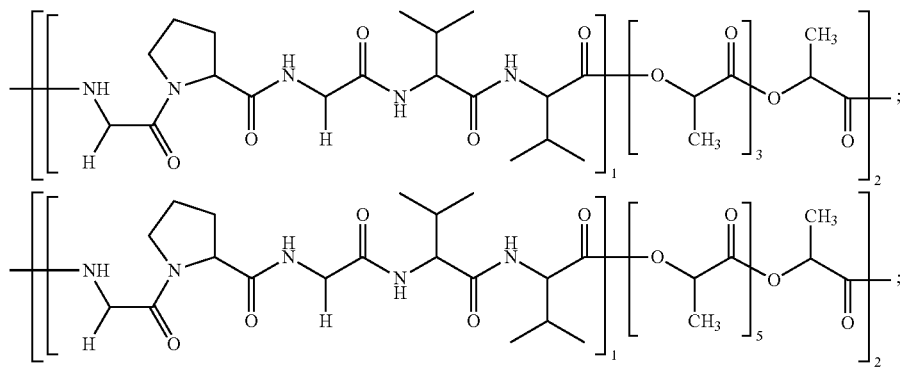

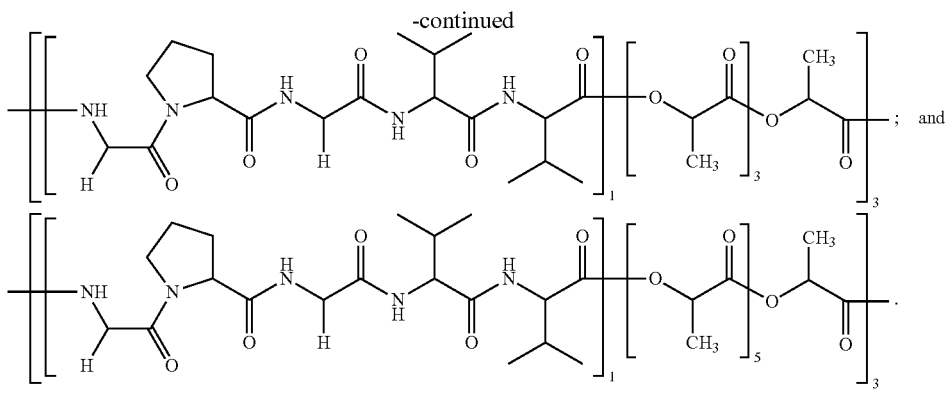
; and

Another embodiment relates to biocompatible polymers having the formula:

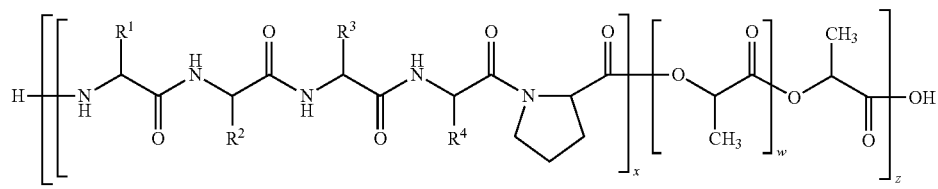

wherein $R^1$, $R^2$, $R^3$, and $R^4$ are each independently chosen from:
  i) hydrogen;
  ii) —$CH_3$;
  iii) —$CH_2CH_3$;
  iv) —$CH_2CH_2CH_3$;
  v) —$CH(CH_3)_2$;
  vi) —$CH(CH_3)CH_2CH_3$; and
  vii) —$CH_2CH_2CH(CH_3)_2$;

the index w is an integer from 0 to 9; the index x is an integer from 1 to 30; and the index z is an integer from 1 to 2000.

One embodiment relates to biocompatible polymers having the formula and which formula includes the ECM an ECM mimetic as set forth in SEQ ID NO: 29:

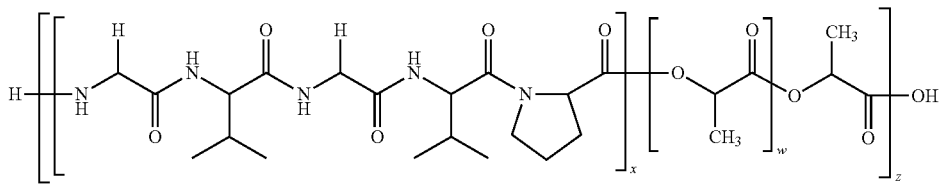

Non-limiting examples of this embodiment include (each comprising SEQ ID NO: 29):

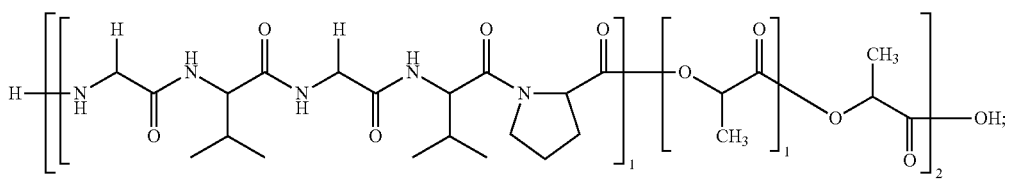

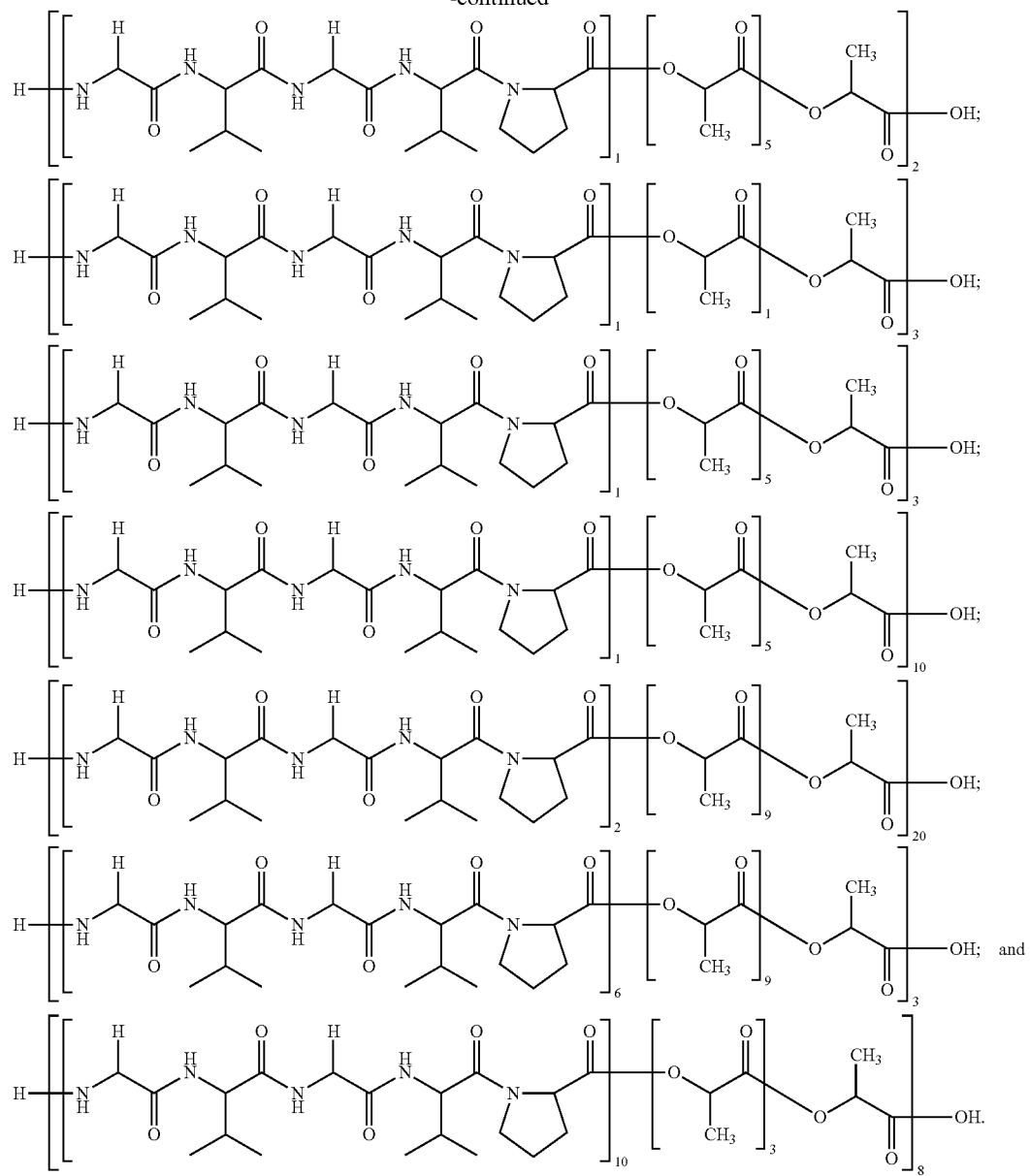
Further embodiments include disclosed polymers having the formulae:
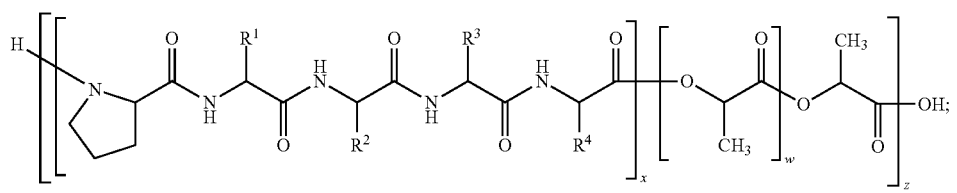

-continued

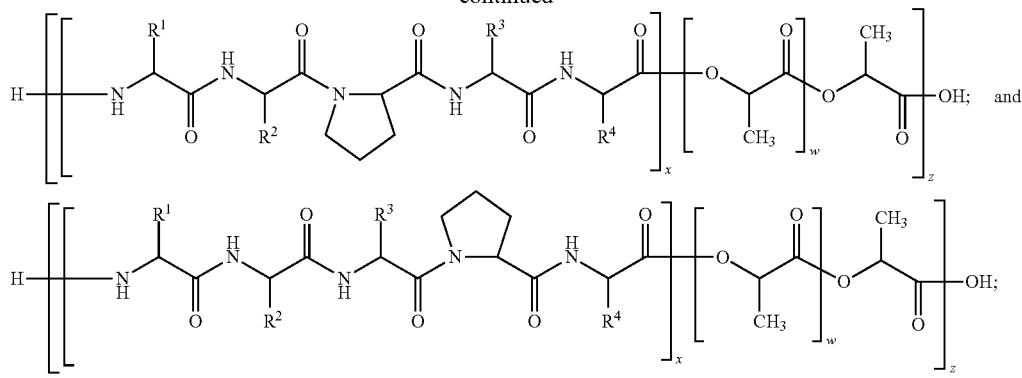

wherein $R^1$, $R^2$, $R^3$, and $R^4$ are each independently chosen from:
i) hydrogen;
ii) —$CH_3$;
iii) —$CH_2CH_3$;
iv) —$CH_2CH_2CH_3$;
v) —$CH(CH_3)_2$;
vi) —$CH(CH_3)CH_2CH_3$; and
vii) —$CH_2CH_2CH(CH_3)_2$;

the index w is an integer from 0 to 9; the index x is an integer from 1 to 30; and the index z is an integer from 1 to 2000.

Uses

The disclosed polymers can be used in a variety of medical, pharmaceutical, medical device, veterinarian applications. Generally, non-limiting examples of applications for the disclosed polymers include the use of these polymers:

(a) As devices including stents, implants, medical devices, medical products and the like including, without being limiting, examples such as stents, implants, films, foams, sponges, patches, matrices, fabrics, meshes, membranes, felts, solids, liquids, viscous liquids, viscoelastic materials, gels, hydrogels, and so on.

(b) As coatings on: stents, implants, devices, medical devices, medical products, and so on.

(c) For delivery or administration of bioactive agents or other medically useful agents including: contrast agents, imaging agents, bioactive agents, drugs, small molecule drugs, peptides, proteins, nucleic acids, antibodies, antibody fragments, factors, aptamers, and so on.

(d) As drug-eluting polymer coatings or films on devices including stents, implants, medical devices, medical products, and so on.

These polymers can be used for delivery or administration of bioactive agents or other medically useful agents from various forms including non-limiting examples such as films, sheets, coatings, particles, microparticles, nanoparticles, capsules, microcapsules, nanocapsules, implants, foams, sponges, patches, matrices, fabrics, meshes, membranes, felts, solids, liquids, viscous liquids, viscoelastic materials, gels, hydrogels, and so on.

The following are non-limiting examples of bioactive agents that can administered using the polymers of the present invention and herein include, but are not limited to, peptides, proteins such as hormones, enzymes, antibodies, monoclonal antibodies, antibody fragments, monoclonal antibody fragments, and the like, nucleic acids such as aptamers, siRNA, DNA, RNA, antisense nucleic acids or the like, antisense nucleic acid analogs or the like, low-molecular weight compounds, or high-molecular-weight compounds, receptor agonists, receptor antagonists, partial receptor agonists, and partial receptor antagonists.

Representative drugs or bioactive agents that can be used in the microparticle composition of the present disclosure include, but are not limited to, peptide drugs, protein drugs, desensitizing materials, antigens, factors, growth factors, anti-infective agents such as antibiotics, antimicrobial agents, antiviral, antibacterial, antiparasitic, antifungal substances and combination thereof, antiallergenics, steroids, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, anti-Alzheimer's agents, antihypertensive agents, beta-adrenergic blocking agents, alpha-adrenergic blocking agents, nutritional agents, and the benzophenanthridine alkaloids. The bioactive agent can further be a substance capable of acting as a stimulant, a sedative, a hypnotic, an analgesic, an anticonvulsant, and the like.

Further, polymers disclosed herein can be used to deliver or administer CNS-active drugs, neuro-active drugs, inflammatory and anti-inflammatory drugs, renal and cardiovascular drugs, gastrointestinal drugs, anti-neoplastics, immuno-modulators, immunosuppressants, hematopoietic agents, growth factors, anticoagulant, thrombolytic, antiplatelet agents, hormones, hormone-active agents, hormone antagonists, vitamins, ophthalmic agents, anabolic agents, antacids, anti-asthmatic agents, anti-cholesterolemic and anti-lipid agents, anti-convulsants, anti-diarrheals, anti-emetics, anti-manic agents, antimetabolite agents, anti-nauseants, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, laxatives, mineral supplements, mucolytic agents, neuromuscular drugs, peripheral vasodilators, psychotropics, stimulants, thyroid and anti-thyroid agents, tissue growth agents, uterine relaxants, vitamins, antigenic materials, and so on. Other classes of bioactive agents include those cited in Goodman & Gilman's The Pharmacological Basis of Therapeutics (McGraw Hill) as well as bioactive agents included in the Merck Index and The Physicians Desk Reference (Thompson Healthcare).

Other bioactive agents include androgen inhibitors, polysaccharides, growth factors (e.g., a vascular endothelial growth factor-VEGF), hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Further examples of bioactive agents include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, antiproliferatives, anti-VEGF agents, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

The controlled release system can comprise a large number of bioactive agents either singly or in combination. Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, paclitaxel, taxol, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxam®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; immunosuppressants such as rapamycin, tacrolimus, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, or a combination thereof. In one aspect, the bioactive agent can be a combination of Rifampicin (Rifampin in U.S.) and Minocycline.

When the disclosed polymers are used to prepare vascular grafts they can have similar characteristics to native vessels while at the same time eliciting a desired biological response, for example, elastin mimetic response. The biocompatible polymers disclosed herein can be used in one or more ways or configurations. In one embodiment, synthetic vascular grafts comprising the disclosed biocompatible polymers can be prepared in varying sizes or lengths using techniques known to those of ordinary skill in the art. For example, fabrication of these synthetic vessels can be achieved using an electrospinning apparatus to shape and form the vascular graft to the desired diameter, thickness, and length. In some iterations the biocompatible polymers can comprise crosslinkable units so that the polymer can be further crosslinked to provide the desired mechanical rigidity, for example, when fabrication arterial grafts.

In another embodiment, natural vascular grafts can be coated with one or more of the disclosed biocompatible polymers. In this embodiment, the polymer coating elicits a biological response that aids in the body's ability to assimilate the graft. Also, the use of ECM-mimetic peptide containing polymers allows for more rapid healing, for example, in the case wherein a mixture of elastin and fibrinogen-mimetic peptides are used.

Further disclosed herein are biomechanical devices that comprise one or more of the biocompatible polymers. For example, stents used in overcoming arterial blockage can be coated with the disclosed polymers in order to elicit one or more desirable responses. These responses can include wound healing or enhancement of arterial wall integrity.

Another embodiment of biomechanical devices relates to joint replacement therapy, for example, hip and knee replacement apparatus. Other biomechanical devices include sutures, for example, arterial sutures. The sutures can comprise the disclosed polymers or standard biocompatible sutures can be coated with the disclosed polymers.

The disclosed biocompatible polymers can be used to form films or membranes. For example, they can be used for tissue regeneration applications when the polymer is fashioned into a membrane or film and used as a patch for tissue reconstruction (e.g., cardiac or bladder tissue reconstruction), skin graft, and the like.

The disclosed biocompatible polymers can also be used a coatings on a medical device. A particularly desirable coating is a drug-eluting coating on a device such as a stent. Alternatively, the disclosed biodegradable polymer can be used to prepare a fully degradable polymer stent (with or without added drug; with or without a drug-eluting polymer coating on top of the degradable polymer stent).

Preparations

The present disclosure further relates to method for preparing the disclosed biocompatible polymers.

Step (a)

Step (a) comprises providing an ECM-mimetic peptide-comprising reagent having the formula:

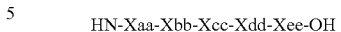

wherein Xaa, Xbb, Xcc, Xdd, and Xee, are each independently an amino acid residue.

A non-limiting example of an ECM-mimetic peptide-comprising reagent is valinylprolinylglycinylvalinylglycine (SEQ ID NO: 13) having the formula:

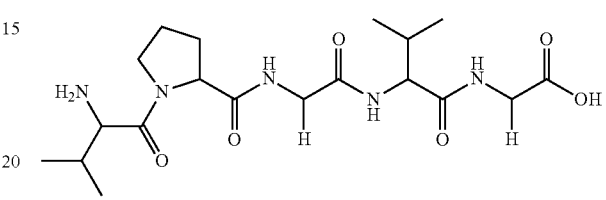

i)
                                        [SEQ ID NO: 2]
Val-Pro-Gly-Gly-Val;

ii)
                                        [SEQ ID NO: 3]
Val-Pro-Val-Gly-Gly;

iii)
                                        [SEQ ID NO: 4]
Gly-Pro-Gly-Val-Val;

iv)
                                        [SEQ ID NO: 5]
Gly-Pro-Val-Gly-Val;

v)
                                        [SEQ ID NO: 6]
Gly-Pro-Val-Val-Gly;

vi)
                                        [SEQ ID NO: 7]
Pro-Val-Gly-Val-Gly;

vii)
                                        [SEQ ID NO: 8]
Pro-Val-Gly-Gly-Val;

viii)
                                        [SEQ ID NO: 9]
Pro-Val-Val-Gly-Gly;

ix)
                                        [SEQ ID NO: 10]
Pro-Gly-Gly-Val-Val;

x)
                                        [SEQ ID NO: 11]
Pro-Gly-Val-Gly-Val;

xi)
                                        [SEQ ID NO: 12]
Pro-Gly-Val-Val-Gly;

xii)
                                        [SEQ ID NO: 13]
Val-Gly-Pro-Val-Gly;

xiii)
                                        [SEQ ID NO: 14]
Val-Gly-Pro-Gly-Val;

xiv)
Val-Val-Pro-Gly-Gly;  [SEQ ID NO: 15]

xv)
Gly-Gly-Pro-Val-Val;  [SEQ ID NO: 16]

xvi)
  [SEQ ID NO: 17]

In one iteration, Step (a) comprises providing an ECM-mimetic peptide-comprising reagent having the formula:
N-(Xaa-Xbb-Xcc-Xdd-Xee)$_x$-OH wherein Xaa, Xbb, Xcc, Xdd, and Xee are each independently an amino acid residue, and the index x is an integer from 1 to 100.

A non-limiting example of an ECM-mimetic peptide-comprising reagent according to this iteration wherein x is equal to 2 is represented by SEQ ID NO: 47 and has the formula:

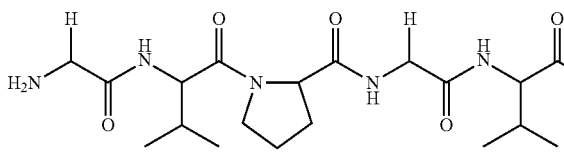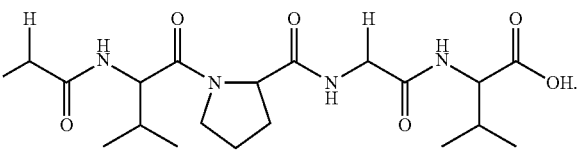

-continued
Gly-Val-Pro-Gly-Val;

xvii)
Gly-Val-Pro-Val-Gly;  [SEQ ID NO: 18]

xviii)
Val-Gly-Val-Pro-Gly;  [SEQ ID NO: 19]

xix)
Val-Gly-Gly-Pro-Val;  [SEQ ID NO: 20]

xx)
Val-Val-Gly-Pro-Gly;  [SEQ ID NO: 21]

xxi)
Gly-Gly-Val-Pro-Val;  [SEQ ID NO: 22]

xxii)
Gly-Val-Gly-Pro-Val;  [SEQ ID NO: 23]

xxiii)
Gly-Val-Val-Pro-Gly;  [SEQ ID NO: 24]

xxiv)
Val-Gly-Val-Gly-Pro;  [SEQ ID NO: 25]

xxv)
Val-Gly-Gly-Val-Pro;  [SEQ ID NO: 26]

xxvi)
Val-Val-Gly-Gly-Pro;  [SEQ ID NO: 27]

xxvii)
Gly-Gly-Val-Val-Pro;  [SEQ ID NO: 28]

xxviii)
Gly-Val-Gly-Val-Pro; and  [SEQ ID NO: 29]

xxix)
Gly-Val-Val-Gly-Pro.  [SEQ ID NO: 30]

The ECM mimetic peptide, Mim, or the polypeptide (Mim)$_x$, can be prepared by known chemical synthesis methods. Preferably, however, the polypeptide (Mim)$_x$ is prepared through known microbial synthetic methods.

Step (b)

Step (b) comprises providing a biodegradable reagent such as a prepolymer that does not comprise an α-amino acid. In one embodiment, the biodegradable reagent can be a homopolymer, copolymer, or block copolymer of a non-α-amino acid comprising monomer. Non-limiting examples include:
  i) poly(lactide);
  ii) poly(glycolide);
  iii) poly(caprolactone);
  iv) poly(valerolactone);
  v) poly(lactide-co-glycolide);
  vi) poly(lactide-co-caprolactone);
  vii) poly(lactide-co-valerolactone);
  viii) poly(glycolide-co-caprolactone);
  ix) poly(glycolide-co-valerolactone);
  x) poly(lactide-co-glycolide-co-caprolactone); and
  xi) poly(lactide-co-glycolide-co-valerolactone).

In a further embodiment, the biodegradable reagent can comprise a single monomeric unit, for example, lactic acid, glycolic acid, 6-hydroxyhexanoic acid, a hydroxy acid, a hydroxy acid fatty acid, and the like, or a reagent that results in the inclusion of a single monomeric unit that incorporates a biodegradable functionality into the polymer backbone. Still further the biodegradable reagent can comprise dimers or trimers of lactic acid and so forth. These reagents can be prepared by methods known in the art or, in some cases, are commercially available.

Step (c)

Step (c) comprises contacting the ECM-mimetic peptide-comprising reagent from step (a) with the biodegradable reagent from step (b) to form a combination of (Mim)$_x$-(Bio-Deg)$_y$. In a further embodiment of step (c), the step involves contacting the ECM-mimetic peptide-comprising reagent from either step (a) or the biodegradable reagent from step (b) with a linking reagent, wherein the linking reagent introduces one or more linking groups or bonds between the ECM-mimetic peptide-comprising reagent and the biodegradable reagent including moieties chosen from:
  i) an alkyl;
  ii) an alkoxy;
  iii) a carbonyl;
  iv) a halogen comprising leaving group;

v) an ester;
vi) an orthoester;
vii) an anhydride;
viii) a phosphate;
ix) a phosphazene;
x) a phosphoester;
xi) a dioxanaone;
xii) a carbonate;
xiii) an orthocarbonate;
xiv) an amide;
xv) an amine;
xvi) an ester amide;
xvii) a isocyanate;
xviii) a urethane;
xix) an etherester;
xx) a pyrrolidone; or
xxi) a unit comprising a combination of units (i) to (xx).

The resulting combination of $(Mim)_x$-$(BioDeg)_y$ can be terminated on one end with either an —$NH_2$ or an —OH group and on the other end by a —COOH group. This facilitates the polymerization in the next step, step (d).

Step (d)

Step (d) involves the polymerization of the $(Mim)_x$-$(BioDeg)_y$ entity formed in step (c). The polymerization reaction can be performed with various synthetic techniques. One method includes a polycondensation reaction where $(Mim)_x$-$(BioDeg)_y$, having either an amine or hydroxyl group on one end and a carboxylic acid group on the other end, reacts. A second method includes the use of peptide coupling reagents to link together amine or hydroxyl end-groups with the carboxylic acid groups. This approach is the one shown Step 3 of the scheme below where EDC is the peptide coupling agent. EDC first activates the carboxylic acid group, which then becomes a reactive site for the hydroxyl end-groups to attack. Successive reactions then are used to form the final biodegradable ECM-mimetic polymer. Thus, the result of step (d) can be described as -(-$(Mim)_x$-$(BioDeg)_y$-)$_z$, where indicia x, y, and z are as defined herein.

In a further embodiment, linking groups, L, can be incorporated into the polymer in various ways. For example, the chemistries described in steps (c) or (d), or both, can involve reactive reagents that are useful in coupling together $Mim_x$ and $BioDeg_y$ (step c) and in preparing the polymer (step d). Such coupling steps can introduce linking groups or bonds to the composition (linking groups "L"). Some reactive reagents useful for performing these coupling steps could include carboxylic acid activating reagents such as: NHS, IIDQ, EDCI, CDI, HOBt, DCCI (for examples, see Principles of Peptide Synthesis, M. Bodanszky, Springer-Verlag, 1984; Amino Acid and Peptide Synthesis ($2^{nd}$ Edition), John Jones, Oxford University Press, 2002), which are often useful in preparing amide bonds through the coupling of carboxylic acids with amine groups and in preparing ester bonds through the coupling of carboxylic acids with hydroxyl groups.

Throughout the specification and claims ECM-mimetics are represented in various ways, however, when possible short-hand notation is used, for example, for the 5-amino acid comprising ECM-mimetic valylprolylglycylvalylglycine [SEQ ID NO:1], the short hand notation VPGVG [SEQ ID NO:1] is used. When describing chemical synthesis of the disclosed polymers alternative representations are used, however, the artisan will know that these representations are used to facilitate the understanding of chemical reactions which can take place at the terminal amino and carboxy terminus of an ECM-mimetic. For example, the formula $H_2N$-[VPGVG]-$CO_2H$ [SEQ ID NO:1] stands equally well for VPGVG [SEQ ID NO:1].

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Prophetic Example 1

Synthesis of an ECM-Mimetic Peptide

Scheme I outlines the preparation of the ECM-mimetic peptide VPGVG [SEQ ID NO:1].

Scheme I

Step (i)
Cbz-NH-[V]-$CO_2H$+$H_2N$-[P]-CO2CH3→Cbz-NH-[VP]-$CO_2CH_3$

Step (ii)
Cbz-NH-[VP]-$CO_2CH_3$→Cbz-NH-[VP]-$CO_2H$

Step (iii)
Cbz-NH-[VP]-$CO_2H$+H2N-[G]-$CO_2CH_3$→Cbz-NH-[VPG]-$CO_2CH_3$

Step (iv)
Cbz-NH-[VPG]-$CO_2CH_3$→Cbz-NH-[VPG]-$CO_2H$

Step (v)
Cbz-NH-[VPG]-$CO_2H$+H2N-[V]-$CO_2CH_3$→Cbz-NH-[VPGV] (SEQ ID NO: 87)-$CO_2CH_3$ Step (vi)
Cbz-NH-[VPGV]] (SEQ ID NO: 87)-$CO_2CH_3$→Cbz-NH-[VPGV]] (SEQ ID NO: 87)-$CO_2H$ Step (vii)
Cbz-NH-[VPGV]] (SEQ ID NO: 87)-$CO_2H$+$H_2N$-[G]-$CO_2CH_3$→Cbz-NH-[VPGVG]] (SEQ ID NO: 1)-$CO_2CH_3$ Step (viii)
Cbz-NH-[VPGVG] (SEQ ID NO: 1)-$CO_2CH_3$→Cbz-NH-[VPGVG]] (SEQ ID NO: 1)-$CO_2H$ Step (ix)
Cbz-NH-[VPGVG] (SEQ ID NO: 1)-$CO_2H$→$H_2N$-[VPGVG]-$CO_2H$ [SEQ ID NO:1]

The pentapeptide $H_2N$-[VPGVG] (SEQ ID NO: 1)-$CO_2H$ can be prepared by other similar synthetic procedures, for example, using standard coupling procedures or using polymer supported (Merrifield) coupling procedures. In other examples, microbial fermentation can be used to prepare the pentapeptide (as well as the polypentapeptide). The following is a non-limiting prophetic example of the preparation of VPGVG [SEQ ID NO:1].

Step (i)

Preparation of N-Cbz-valylproline methyl ester (Cbz-NH-[VP]-CO$_2$CH$_3$): To a solution of N-Cbz-valine (2.5 g, 10 mmol), 1-(3-dimethylaminopropyl)-3-ethylcarbodiimide (1.6 g, 11 mmol) and triethylamine (2.0 g, 20 mmol) in DMF (10 mL) is added dropwise a solution of proline methyl ester hydrochloride (1.8 g, 11 mmol) in DMF (5 mL). The solution is stirred at room temperature and the reaction monitored by TLC until the disappearance of N-Cbz-valine. The reaction solution is then diluted with dichloromethane (30 mL) and the organic layer is extracted with 0.1 N HCl (20 mL), water (20 mL), then dried over Na$_2$SO$_4$. The solvent is removed in vacuo to afford the desired compound.

Step (ii)

Preparation of N-Cbz-valylproline (Cbz-NH-[VP]-CO$_2$H): To a solution of N-Cbz-valylproline methyl ester (Cbz-NH-[VP]-CO$_2$CH$_3$) (3.62 g, 10 mmol) in THF (10 mL) is added a 1M aqueous solution of LiOH (11 mL, 11 mmol) and the solution is stirred overnight. The resulting solution is acidified to pH about 7 with 1M HCl and the contents of the flask partitioned between water (20 mL) and ethyl acetate (20 mL). The organic phase is extracted with brine, dried over Na$_2$SO$_4$ then concentrated in vacuo to afford the desired compound.

Step (iii)

Preparation of N-Cbz-valylprolylglycine methyl ester (Cbz-NH-[VPG]-CO$_2$CH$_3$): To a solution of N-Cbz-valylproline (Cbz-NH-[VP]-CO$_2$H) (3.5 g, 10 mmol), 1-(3-dimethylamino-propyl)-3-ethylcarbodiimide (1.6 g, 11 mmol) and triethylamine (2.0 g, 20 mmol) in DMF (15 mL) is added dropwise a solution of glycine methyl ester hydrochloride (1.38 g, 11 mmol) in DMF (5 mL). The solution is stirred at room temperature and the reaction monitored by TLC until the disappearance of N-Cbz-valylproline. The reaction solution is then diluted with dichloromethane (50 mL) and the organic layer is extracted with 0.1 N HCl (20 mL), water (20 mL), then dried over Na$_2$SO$_4$. The solvent is removed in vacuo to afford the desired compound.

Step (iv)

Preparation of N-Cbz-valylprolylglycine (Cbz-NH-[VPG]-CO$_2$H): To a solution of N-Cbz-valylprolylglycine methyl ester (Cbz-NH-[VPG]-CO$_2$CH$_3$) (4.2 g, 10 mmol) in THF (20 mL) is added a 1M aqueous solution of LiOH (11 mL, 11 mmol) and the solution is stirred overnight. The resulting solution is acidified to pH about 7 with 1M HCl and the contents of the flask partitioned between water (30 mL) and ethyl acetate (30 mL). The organic phase is extracted with brine, dried over Na$_2$SO$_4$ then concentrated in vacuo to afford the desired compound.

Step (v)

Preparation of N-Cbz-valylprolylglycylvaline methyl ester (Cbz-NH-[VPGV] (SEQ ID NO: 87)-CO$_2$CH$_3$): To a solution of N-Cbz-valylprolylglycine (Cbz-NH-[VPG]-CO$_2$H) (4.05 g, 10 mmol), 1-(3-dimethylaminopropyl)-3-ethylcarbodiimide (1.6 g, 11 mmol) and triethylamine (2.0 g, 20 mmol) in DMF (15 mL) is added dropwise a solution of valine methyl ester hydrochloride (1.8 g, 11 mmol) in DMF (5 mL). The solution is stirred at room temperature until the disappearance of N-Cbz-valylprolylglycine. The reaction solution is then diluted with dichloromethane (50 Ml) and the organic layer is extracted with 0.1 N HCl (20 mL), water (20 mL), then dried over Na$_2$SO$_4$. The solvent is removed in vacuo to afford the desired compound.

Step (vi)

Preparation of N-Cbz-valylprolylglycylvaline (Cbz-NH-[VPGV] (SEQ ID NO: 87)-CO$_2$H): To a solution of N-Cbz-valylprolylglycylvaline methyl ester (Cbz-NH-[VPGV] (SEQ ID NO: 87)-CO$_2$CH$_3$) (5.2 g, 10 mmol) in THF (25 mL) is added a 1M aqueous solution of LiOH (11 mL, 11 mmol) and the solution is stirred overnight. The resulting solution is acidified to pH about 7 with 1M HCl and the contents of the flask partitioned between water (30 Ml) and ethyl acetate (30 mL). The organic phase is extracted with brine, dried over Na$_2$SO$_4$ then concentrated in vacuo to afford the desired compound.

Step (vii)

Preparation of N-Cbz-valylprolylglycylvalylglycine methyl ester (Cbz-NH-[VPGVG] (SEQ ID NO: 1)-CO$_2$CH$_3$): To a solution of N-Cbz-valylprolylglycylvaline (Cbz-NH-[VPGV] (SEQ ID NO: 87)-CO$_2$H) (5.54 g, 10 mmol), 1-(3-dimethylaminopropyl)-3-ethylcarbodiimide (1.6 g, 11 mmol) and triethylamine (2.0 g, 20 mmol) in DMF (15 mL) is added dropwise a solution of glycine methyl ester hydrochloride (1.38 g, 11 mmol) in DMF (5 mL). The solution is stirred at room temperature until the disappearance of N-Cbz-valylprolylglycylvaline. The reaction solution is then diluted with dichloromethane (50 mL) and the organic layer is extracted with 0.1 N HCl (20 mL), water (20 mL), then dried over Na$_2$SO$_4$. The solvent is removed in vacuo to afford the desired compound.

Step (viii)

Preparation of N-Cbz-valylprolylglycylvalylglycine (Cbz-NH-[VPGVG] (SEQ ID NO: 1)-CO$_2$H): To a solution of N-Cbz-valylprolylglycylvalylglycine methyl ester (Cbz-NH-[VPGVG] (SEQ ID NO: 1)-CO$_2$CH$_3$): (5.75 g, 10 mmol) in THF (30 mL) is added a 1M aqueous solution of LiOH (11 mL, 11 mmol) and the solution is stirred overnight. The resulting solution is acidified to pH about 7 with 1M HCl and the contents of the flask partitioned between water (25 mL) and ethyl acetate (50 mL). The organic phase is extracted with brine, dried over Na$_2$SO$_4$ then concentrated in vacuo to afford the desired compound.

Step (ix)

Preparation of valylprolylglycylvalylglycine (H$_2$N-[VPGVG]-CO$_2$H) [SEQ ID NO:1]: N-Cbz-valylprolylglycylvalylglycine (Cbz-NH-[VPGVG] (SEQ ID NO: 1)-CO$_2$H) (5.5 g, 10 mmol) in methanol (100 mL) is charged to a 500 mL Parr hydrogenation vessel. 10% Pd/C (10 mg) is added under nitrogen atmosphere. The solution is hydrogenated for 3 hours under 45 psi of hydrogen gas with sufficient shaking to insure complete dispersion of the catalyst. The nitrogen purged solution is then filtered through Celite™ to remove the catalyst. The filtrate is concentrated in vacuo to afford the desired product.

Prophetic Example 2

Synthesis of an ECM-Mimetic Peptide

Scheme II outlines the preparation of [VPGVG]$_2$ [SEQ ID NO:31] as described in Example 2 herein below.

Scheme II

Step (i)
Cbz-NH-[VPGVG] (SEQ ID NO: 1)-CO$_2$CH$_3$→H$_2$N-[VPGVG]-CO$_2$CH$_3$
Step (ii)
Cbz-NH-[VPGVG]-CO$_2$H+H$_2$N-[VPGVG] (SEQ ID NO: 1)-CO$_2$CH$_3$→Cbz-NH-[VPGVG]$_2$-CO$_2$CH$_3$ Step (iii)
Cbz-NH-[VPGVG]$_2$(SEQ ID NO: 31)-CO$_2$CH$_3$→Cbz-NH-[VPGVG]$_2$-CO$_2$H Step (iv)
Cbz-NH-[VPGVG]$_2$(SEQ ID NO: 31)-CO$_2$H→H$_2$N-[VPGVG]$_2$-CO$_2$H [SEQ ID NO:31]

The pentapeptide H$_2$N-[VPGVG]$_2$-CO$_2$H [SEQ ID NO:31] can be prepared by other techniques. The following is a non-limiting prophetic example of the preparation of H$_2$N-[VPGVG]$_2$-CO$_2$H [SEQ ID NO:31].

Step (i)
Preparation of valylprolylglyclyvalylglycine methyl ester (H$_2$N-[VPGVG] (SEQ ID NO: 1)-CO$_2$CH$_3$): N-Cbz-valyl-prolyl-glycylvalylglycine methyl ester (Cbz-NH-[VPGVG] (SEQ ID NO: 1)-CO$_2$CH$_3$) (5.75 g, 10 mmol) in methanol (100 mL) is charged to a 500 mL Parr hydrogenation vessel. 10% Pd/C (10 mg) is added under nitrogen blanketing. The solution is hydrogenated for 3 hours under 45 psi of hydrogen gas with sufficient shaking to insure complete dispersion of the catalyst. The nitrogen purged solution is then filtered through Celite™ to remove the catalyst. The filtrate is concentrated in vacuo to afford the desired product.

Step (ii) Preparation of N-Cbz-valylprolylglycylvalylgly-cylvalylprolylglycylvalylglycine methyl ester (Cbz-NH-[VPGVG]$_2$(SEQ ID NO: 31)-CO$_2$CH$_3$): To a solution of N-Cbz-valylprolylglycylvalylglycine (Cbz-NH-[VPGVG] (SEQ ID NO: 1)-CO$_2$H) (5.6 g, 10 mmol) [as prepared in step (h) of Scheme I herein above], 1-(3-dimethylaminopropyl)-3-ethylcarbodiimide (1.6 g, 11 mmol) and triethylamine (2.0 g, 20 mmol) in DMF (30 mL) is added dropwise a solution of valylprolylglycylvalyl-glycine methyl ester (H$_2$N-[VPGVG] (SEQ ID NO: 1)-CO$_2$CH$_3$) (4.85 g, 11 mmol) in DMF (20 mL). The solution is stirred at room temperature and the reaction monitored by TLC until the disappearance of N-Cbz-valylprolylglycylvalylglycine. The reaction solution is then diluted with dichloromethane (50 mL) and the organic layer is extracted with 0.1 N HCl (20 mL), water (20 mL), then dried over Na$_2$SO$_4$. The solvent is removed in vacuo to afford the desired compound.

Step (iii)
Preparation of N-Cbz-valylprolylglycylvalylgly-cylvalylprolylglycylvalylglycine (Cbz-NH-[VPGVG]$_2$ (SEQ ID NO: 31)-CO$_2$H): To a solution of N-Cbz-valylprolylgly-cylvalylglycylvalyl-prolylglycylvalylglycine methyl ester (Cbz-NH-[VPGVG]$_2$ (SEQ ID NO: 31)-CO$_2$CH$_3$) (9.8 g, 10 mmol) in THF (50 mL) is added a 1M aqueous solution of LiOH (11 mL, 11 mmol) and the solution is stirred overnight. The resulting solution is acidified to pH about 7 with 1M HCl and the contents of the flask partitioned between water (50 mL) and ethyl acetate (50 mL). The organic phase is extracted with brine, dried over Na$_2$SO$_4$ then concentrated in vacuo to afford the desired compound.

Step (iv)
Preparation of valylprolylglycylvalylgly-cylvalylprolylglycylvalylglycine [VPGVG]$_2$ (SEQ ID NO: 31) (H$_2$N-[VPGVG]$_2$-CO$_2$H) [SEQ ID NO:31]: To a solution of N-Cbz-valylprolylglycylvalyl-glycylvalylprolylglycylva-lylglycine (Cbz-NH-[VPGVG]$_2$ (SEQ ID NO: 31)-CO$_2$H) (8.5 g, 10 mmol) in methanol (100 mL) is charged to a 500 mL Parr hydrogenation vessel. 10% Pd/C (10 mg) is added. The solution is hydrogenated for 3 hours under 45 psi of hydrogen gas with sufficient shaking to insure complete dispersion of the catalyst. The nitrogen purged solution is then filtered through Celite™ to remove the catalyst. The filtrate is concentrated in vacuo to afford the desired product.

Prophetic Example 3

Synthesis of an ECM-Mimetic Peptide

Scheme III outlines the preparation of [VPGVG]$_5$ [SEQ ID NO: 90] using the procedures as described in Example 2.

Scheme III

Step (i)
Cbz-NH-[VPGVG]$_2$ (SEQ ID NO: 31)-CO$_2$H+H$_2$N-[VPGVG] (SEQ ID NO: 1)-CO$_2$CH$_3$→Cbz-NH-[VPGVG]$_3$ (SEQ ID NO: 88)-CO$_2$CH$_3$ Step (ii)
Cbz-NH-[VPGVG]$_3$(SEQ ID NO: 88)-CO$_2$CH$_3$→Cbz-NH-[VPGVG]$_3$(SEQ ID NO: 88)-CO$_2$H Step (iii)
Cbz-NH-[VPGVG]$_3$(SEQ ID NO: 88)-CO$_2$H+H2N-[VPGVG] (SEQ ID NO: 1)-CO$_2$CH$_3$→Cbz-NH-[VPGVG]$_4$ (SEQ ID NO: 89)-CO$_2$CH$_3$ Step (iv)
Cbz-NH-[VPGVG]$_4$ (SEQ ID NO: 89)-CO$_2$CH$_3$→Cbz-NH-[VPGVG]$_4$(SEQ ID NO: 89)-CO$_2$H Step (v)
Cbz-NH-[VPGVG]$_4$ (SEQ ID NO: 89)-CO$_2$H+H$_2$N-[VPGVG] (SEQ ID NO: 1)-CO$_2$CH$_3$→Cbz-NH-[VPGVG]$_5$ (SEQ ID NO: 90)-CO$_2$CH$_3$ Step (vi)
Cbz-NH-[VPGVG]$_5$ (SEQ ID NO: 90)-CO$_2$CH$_3$→Cbz-NH-[VPGVG]$_5$ (SEQ ID NO: 90)-CO$_2$H Step (vii)
Cbz-NH-[VPGVG]$_5$ (SEQ ID NO: 90)-CO$_2$H→H$_2$N-[VPGVG]$_5$-CO$_2$H [SEQ ID NO: 90]

Prophetic Example 4

Synthesis of a Biocompatible Biodegradable Polymer as Disclosed Herein

Scheme IV outlines the preparation of a biodegradable elastomeric polymer [VPGVG]$_5$ (SEQ ID NO: 90)-lactate using Cbz-NH-[VPGVG]$_5$ (SEQ ID NO: 90)-CO$_2$H as the starting material, which can be prepared as outlined in Scheme III using the procedures outlined in Scheme II and described in Example 2.

Scheme IV

Step (i)
Cbz-NH-[VPGVG]$_5$ (SEQ ID NO: 90)-CO$_2$H+CH$_3$CH(OH)CO$_2$CH$_3$→Cbz-NH-[VPGVG]$_5$ (SEQ ID NO: 90)-CO$_2$CH(CH$_3$)CO$_2$CH$_3$ Step (ii)
Cbz-NH-[VPGVG]$_5$ (SEQ ID NO: 90)-CO$_2$CH(CH$_3$)CO$_2$CH$_3$→Cbz-NH-[VPGVG]$_5$ (SEQ ID NO: 90)-CO$_2$CH(CH$_3$)CO$_2$H Step (iii)
Cbz-NH-[VPGVG]$_5$(SEQ ID NO: 90)-CO$_2$CH(CH$_3$)CO$_2$H→H$_2$N-[VPGVG]$_5$ (SEQ ID NO: 90)-CO$_2$CH(CH$_3$)CO$_2$H Prophetic Example 5

Synthesis of a Biocompatible Biodegradable Polymer as Disclosed Herein

The following is a prophetic example of the synthesis of the biocompatible biodegradable polymer H$_2$N-[VPGVG]$_5$ (SEQ ID NO: 90)-lactate.

Step (i)

Preparation of Cbz-NH-[VPGVG]₅ (SEQ ID NO: 90)-CO₂CH(CH₃)CO₂CH₃: To a solution of N-Cbz-[VPGVG]₅ (SEQ ID NO: 90)-CO₂H (2.24 g, 1 mmol) in DMF (30 mL) is added 1,1'-carbonyldiimidazole (0.32 g, 2 mmol). The reaction solution is cooled in an ice bath and a solution of methyl lactate (0.21 g, 2 mmol) in DMF (2 mL) is added. The reaction is followed by TLC until the disappearance of the acid. The reaction solution is partitioned between water and ethyl acetate/dichloromethane (3:1) (20 mL). The solution is washed with additional water (10 mL aliquots) until the disappearance of methyl lactate. The organic phase is dried and concentrated to afford the desired product.

Step (ii)

Preparation of Cbz-NH-[VPGVG]₅ (SEQ ID NO: 90)-CO₂CH(CH₃)CO₂H: To a solution of Cbz-NH-[VPGVG]₅ (SEQ ID NO: 90)-CO₂CH(CH₃)CO₂CH₃ (2.3 g, 1 mmol) in THF (30 mL) is added a 1M aqueous solution of LiOH (1.1 mL, 1.1 mmol) and the solution is stirred overnight. The resulting solution is acidified to Ph about 7 with 1M HCl and the contents of the flask partitioned between water (50 Ml) and ethyl acetate (50 mL). The organic phase is extracted with brine, dried over Na₂SO₄ then concentrated in vacuo to afford the desired compound.

Step (iii)

Preparation of H₂N-[VPGVG]₅ (SEQ ID NO: 90)-CO₂CH(CH₃)CO₂H: To a solution of Cbz-NH-[VPGVG]₅ (SEQ ID NO: 90)-CO₂CH(CH₃)CO₂H (2.25 g, 1 mmol) in methanol (100 mL) is charged to a 500 mL Parr hydrogenation vessel. 10% Pd/C (10 mg) is added. The solution is hydrogenated for 3 hours under 45 psi of hydrogen gas with sufficient shaking to insure complete dispersion of the catalyst. The nitrogen purged solution is then filtered through Celite™ to remove the catalyst. The filtrate is concentrated in vacuo to afford the desired product.

Prophetic Example 7

Synthesis of a Biocompatible Biodegradable Polymer as Disclosed Herein

The following is a prophetic example of the synthesis of the biocompatible biodegradable polymer -[-NH-[VPGVG]₅ (SEQ ID NO: 90)-CO₂CH(CH₃)CO—]_z-. A solution of H₂N-[VPGVG]₅(SEQ ID NO: 90)-CO₂CH(CH₃)CO₂H (1 g) in THF is stirred for 4 days at room temperature. The resulting solution is concentrated in vacuo and the resulting material taken up in solvent and the average molecular weight is determined.

Prophetic Example 8

Synthesis of a Biocompatible Biodegradable Polymer as Disclosed Herein

Commercially available elastin is filtered and extracted with water. The water soluble fraction is then lyophilized and the peptide fraction obtained is used as the ECM-mimetic, Mim. The Mim portion is taken up in DMF. To this solution in portions is added a mixture of methyl lactate and 1,1'-carbonyldiimidazole (1:1) in DMF. The lactate solution is added until the disappearance of the major original Mim peaks as monitored by HPLC. The resulting solution is partitioned between water and ethyl acetate. The solvent is removed in vacuo and the residue taken up in aqueous THF. A 1M solution of LiOH is added based upon the amount of methyl lactate that was added in the previous step. The solution is neutralized and concentrated. The resulting slurry is filtered to remove any inorganic salts and the filtrate is lyophilized. The resulting solid is taken up in dioxane and heated at 40° C. for 1 week. The solution is concentrated under high vacuum, taken up in water, filtered, and the filtrate lyophilized to provide the desired polymer.

Example 9

Synthesis of a Biocompatible Biodegradable Polymer as Disclosed Herein

Scheme V outlines the synthesis of a biocompatible biodegradable poly (GVGVP) (SEQ ID NO: 29) polymer.

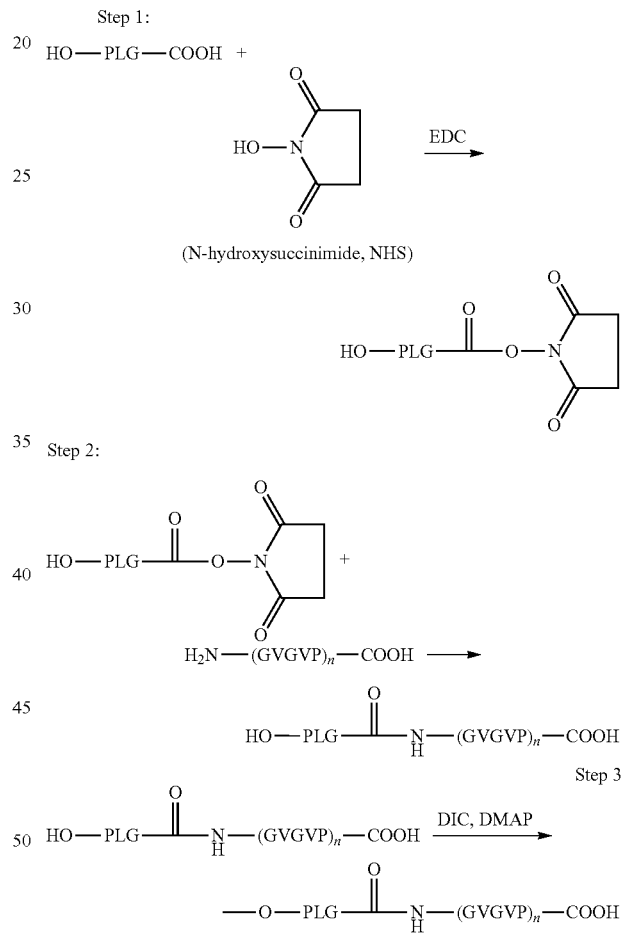

Step 1: Preparation of PLG-NHS

To a single-neck reaction flask, HO-PLG-COOH 5.00 grams (MW 3200, 1.56 mmol of —COOH group), EDC.HCl 2.995 grams (MW 191.7, 15.6 mmole), N-hydroxysuccinimide 1.798 grams (MW 115.09, 15.62 mmol) and 25 mL of chloroform were added. The solid slowly dissolved. The clear solution was stirred at room temperature for 21 hours. The reaction mixture was concentrated by removing about 15 mL of chloroform under high vacuum. About 10 mL of chloroform was left in the flask. To this, 100 mL of methanol was added. The product precipitated. The mixture was stirred for two hours. The supernatant was decanted followed by the addition of 50 mL of fresh methanol. The mixture was stirred overnight. The supernatant was decanted. The solid in the flask was dried under high vacuum at 60° C. 4.15 grams of product PLG-NHS was obtained. The $^1$H NMR indicates the molecular weight to be 3200 Da.

Prophetic Step 2

Preparation of PLG-GVGVP (SEQ ID NO: 91) Conjugate

To a flask, 0.4 grams of GVGVP (SEQ ID NO: 29) (MW 10k, 4×10$^{-5}$ mole), 1.28 grams of PLG-NHS (MW 3200, determined by NMR, 4×10$^{-4}$ mole), and 2 mL of anhydrous DMSO is added. The clear reaction mixture is stirred for 18 hours. To the reaction mixture, 22 mL of ethyl acetate is added. The precipitation of product should occur immediately. The reaction mixtures is transferred to a falcon tube and centrifuged for 20 minutes at 2000 rpm to separate the solid product. The supernatant is decanted and 10 mL of fresh ethyl acetate is added followed by centrifugation. After decanting the supernatant, the solid product is recovered and dried under high vacuum at 60° C. for 3 hours.

Prophetic Step 3

Polycondensation of PLG-GVGVP (SEQ ID NO: 91)

To a flask, 0.52 g of the PLG-GVGVP (SEQ ID NO: 91), 62.μl of diisopropylcarbodiimide (4×10$^{-5}$ mole), 47 mg (3.84×10$^{-5}$ mole) dimethylaminopyridine, and 20 mL of anhydrous DMSO is added. The reaction mixture is stirred at room temperature for 44 hours. To the reaction mixture, 200 mL of ethyl acetate is added. The reaction mixtures is transferred to the falcon tubes and centrifuged for 20 minutes at 2000 rpm to separate the solid product. The supernatant is decanted and 10 mL of fresh ethyl acetate is added. The mixture is stirred for 30 minutes. The mixture is centrifuged again followed by the decantation of the supernatant. The solid product from the tube is dried under high vacuum overnight.

Prophetic Example 10

Coated Stent with Paclitaxel or Rapamycin

The disclosed biocompatible biodegradable polymers can be dissolved in a suitable solvent to which is added a bioactive agent. The agent can be dissolved or dispersed. Examples include paclitaxel or rapamycin. For example, a solution is prepared containing 1-5 wt % polymer in solvent. To this solution is added 1-5 wt % paclitaxel (based on total combined weight drug and polymer). Alternatively, approximately 20-30 wt % rapamycin can be added to the polymer solution (based on total combined weight drug and polymer). A cardiac stent is dipped into the polymer solution containing drug and then removed. The solvent is allowed to dry by evaporation under suitable temperature and pressure conditions to evaporate the solvent leaving behind a drug-containing polymer film coating. The result is a drug-eluting polymer-coated stent. Alternatively, the drug-polymer solution may be spray-coated on to the stent in order to prepare the drug-eluting polymer-coated stent.

Prophetic Example 11

Incorporation of Goserelin Acetate

The disclosed biocompatible biodegradable polymers can be dissolved in a suitable organic solvent system. To this solution is added 5 wt % goserelin acetate (a bioactive peptide). This polymer solution is emulsified under high-shear mixing into an aqueous solution containing 2 wt % polyvinyl alcohol. The resulting oil-in-water suspension is then diluted with additional water to extract the organic solvent from the droplets thereby forming drug-containing polymer microparticles. These particles are collected by filtration, washed, dried to form biodegradable drug-containing microparticles.

Prophetic Example 12

Incorporation of Risperidone

The disclosed biocompatible biodegradable polymers in a dry powdered form can be admixed with dry drug powder to form a dry-blend of drug and polymer. For example, risperidone is blended at a level of 5 wt % into the polymer of the present invention. This blend is then extruded in the form of a 1-mm diameter extruded rod which is then cut to 1.5 cm lengths to form individual dosage forms of an extruded rod implant.

Prophetic Example 13

Preparation of Thin Filaments

The disclosed biocompatible biodegradable polymers can be extruded into a thin filament (approximate 75-100 micrometers in diameter). This filament is then woven to prepare a gauze-like fabric. This fabric is then cut to desired size and used as a wound-cover patch. Alternatively, the thin filament is used to prepare a non-woven felt approximately 0.5 mm in thickness. This felt is cut to desired size and used as a medical/surgical space-filling packing material. Alternatively, the thin filament is prepared containing a suitable quantity of bioactive agent within the filament (for example, 2-5 wt % local anesthetic or 1-5 wt % non-steroidal anti-inflammatory agent). This filament is then used to prepare a woven or non-woven fabric for various medical or surgical applications.

What is claimed is:

1. A biocompatible polymer comprising:
   a) one or more ECM-mimetic peptides having the amino acid sequence GVGVP as set forth in SEQ ID NO: 29; and
   b) one or more biodegradable moieties, wherein the moieties do not comprise an amino acid or residue thereof; wherein the polymer has a weight-average molecular weight of from about 1,000 Da to about 2,000,000 Da.

2. A biocompatible polymer comprising:
   a) one or more ECM-mimetic peptides; and
   b) one or more biodegradable moieties, wherein the moieties do not comprise an amino acid or residue thereof; wherein the polymer has a weight-average molecular weight of from about 1,000 Da to about 2,000,000 Da having the formula:

i)

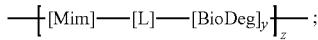

ii)

iii)

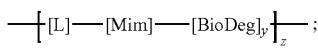

iv)

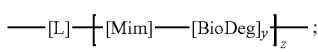

v)

; or iv)

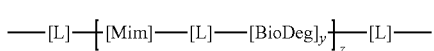

wherein:
Mim is the ECM-mimetic peptide having the formula:

-[Xaa-Xbb-Xcc]$_x$; or

-[Xaa-Xbb-Xcc-Xdd]$_x$; or

-[Xaa-Xbb-Xcc-Xdd-Xee]$_x$; or

-[Xaa-Xbb-Xcc-Xdd-Xee-Xff]$_x$; or

-[Xaa-Xbb-Xcc-Xdd-Xee-Xff-Xgg]$_x$; or

-[Xaa-Xbb-Xcc-Xdd-Xee-Xff-Xgg-Xhh]$_x$; or

-[Xaa-Xbb-Xcc-Xdd-Xee-Xff-Xgg-Xhh-Xii]$_x$; or

-[Xaa-Xbb-Xcc-Xdd-Xee-Xff-Xgg-Xhh-Xii-Xjj]$_x$; or

-[Xaa-Xbb-Xcc-Xdd-Xee-Xff-Xgg-Xhh-Xii-Xjj-Xkk]$_x$;

wherein:
at least one of Xaa, Xbb, Xcc, Xdd, Xee, Xff, Xgg, Xhh, Xii, Xjj, and Xkk is a proline residue; the balance of Xaa, Xbb, Xcc, Xdd, Xee, Xff, Xgg, Xhh, Xii, Xjj, and Xkk are independently chosen from glycine, alanine, valine, leucine, and isoleucine;
wherein BioDeg is the non-amino acid or residue thereof containing one or more biodegradable moieties;
the index x is an integer from 1 to 30;
the index y is an integer from 1 to 10;
the index z is an integer from 1 to 2000;
wherein L is a biodegradable or non-biodegradable linker;
and wherein the one or more ECM-mimetic peptides are chosen from:

i)   Gly-Val-Pro-Gly-Val-Gly-Gly;                    [SEQ ID NO: 61]

ii)  Pro-Gly-Val-Pro-Gly-Val-Gly-Gly;                [SEQ ID NO: 62]

iii) Gly-Val-Pro-Gly-Val-Gly-Leu-Ala;                [SEQ ID NO: 63]

iv)  Val-Gly-Val-Pro-Gly-Val-Gly-Ile-Gly;            [SEQ ID NO: 64]

v)   Gly-Val-Gly-Val-Pro-Gly-Val-Gly-Gly;            [SEQ ID NO: 65]

vi)  Gly-Val-Pro-Gly-Val-Gly-Leu-Leu;                [SEQ ID NO: 66]

-continued vii) Gly-Gly-Gly-Val-Pro-Gly-Val-Gly-Gly-Gly; [SEQ ID NO: 67]

viii) Gly-Gly-Val-Pro-Gly-Val-Gly-Gly-Ala-Ala; [SEQ ID NO: 68]

ix) Pro-Pro-Gly-Val-Pro-Gly-Val-Gly-Gly-Gly-Pro; [SEQ ID NO: 69]

x) Ala-Val-Pro-Gly-Val-Gly-Ala; [SEQ ID NO: 70]

xi) Ala-Ala-Val-Pro-Gly-Val-Gly-Ala; [SEQ ID NO: 71]

xii) Ala-Val-Pro-Gly-Val-Gly-Ala-Ala; [SEQ ID NO: 72]

xiii) Ala-Ala-Val-Pro-Gly-Val-Gly-Ala-Ala; [SEQ ID NO: 73]

xiv) Ala-Leu-Ala-Val-Pro-Gly-Val-Gly-Ala; [SEQ ID NO: 74]

xv) Ala-Val-Pro-Gly-Val-Gly-Ala-Ile-Ile; [SEQ ID NO: 75]

xvi) Gly-Val-Gly-Val-Pro-Gly-Val-Gly-Gly-Val; [SEQ ID NO: 76]

xvii) Ala-Ala-Val-Pro-Gly-Val-Gly-Ala-Ala-Ala; [SEQ ID NO: 77]

xviii) Ala-Ala-Ala-Val-Pro-Gly-Val-Gly-Ala-Ala-Ala; [SEQ ID NO: 78]

and xix) Gly-Val-Gly-Val-Pro; . [SEQ ID NO: 29]

3. The polymer according to claim 2, wherein the linker has the formula:

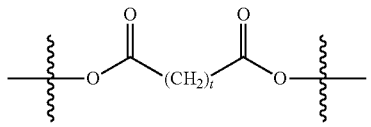

and the index t is an integer from 1 to 10.

4. The polymer according to claim 2, wherein the linker has the formula:

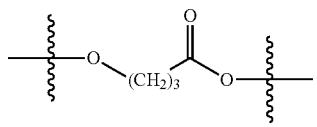

and the index t is from 1 to 10.

5. The polymer according to claim 2, wherein the linker has the formula:

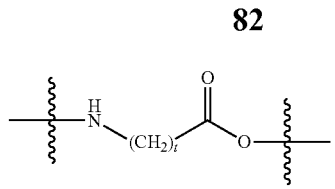

and the index t is from 1 to 10.

6. The polymer according to claim 2, wherein the linker has the formula:

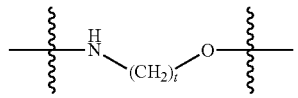

and the index t is from 1 to 10.

7. The polymer according to claim 2, wherein the linker has the formula:

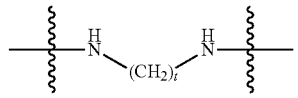

and the index t is from 1 to 10.

8. The polymer according to claim 2, wherein the linker has the formula:

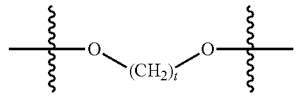

and the index t is from 1 to 10.

9. The polymer according to claim 2, wherein the linker has the formula:

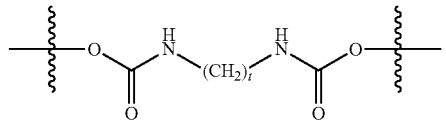

and the index t is from 1 to 10.

10. A method for preparing a biocompatible polymer comprising:
   i) one or more ECM-mimetic peptides having the amino acid sequence GVGVP as set forth in SEQ ID No: 29; and
   ii) one or more biodegradable moieties, wherein the moieties do not comprise an amino acid or residue thereof;
   wherein the polymer has a weight-average molecular weight of from about 1,000 Da to about 2,000,000 Da, comprising:
   a) providing an ECM-mimetic peptide-comprising reagent having the formula:

H$_2$N-G-V-G-V-P-OH [SEQ ID No: 29];

b) coupling a biodegradable reagent that does not comprise an amino acid or residue thereof to the ECM-mimetic peptide-comprising reagent of step (a); and
   c) polymerizing the product of step (b).

11. A method for preparing a biocompatible polymer comprising:
  i) one or more ECM-mimetic peptides having the amino acid sequence GVGVP as set forth in SEQ ID No: 29; and
  ii) one or more biodegradable moieties, wherein the moieties do not comprise an amino acid or residue thereof;
  wherein the polymer has a weight-average molecular weight of from about 1,000 Da to about 2,000,000 Da, comprising:
  a) providing an ECM-mimetic peptide-comprising reagent having the formula:

$H_2N\text{-}(G\text{-}V\text{-}G\text{-}V\text{-}P)_x\text{-}OH$ [SEQ ID No: 29];

and the index x is an integer from 1 to 100;
  b) coupling a biodegradable reagent that does not comprise an amino acid or residue thereof to the ECM-mimetic peptide-comprising reagent of step (a); and
  c) polymerizing the product of step (b).

12. An article comprising the biocompatible polymer of claim 2.

13. The article of claim 12, wherein the article is a stent, implant, film, foam, sponge, patch, matrix, fabric, mesh, membrane, or felt.

14. The article of claim 12, wherein the article is a stent that is coated with the biocompatible polymer.

15. The article of claim 14, further comprising a bioactive agent.

* * * * *